United States Patent
Pasquino et al.

(10) Patent No.: US 10,702,252 B2
(45) Date of Patent: Jul. 7, 2020

(54) DEVICE AND METHOD FOR TRANSCATHETER HEART VALVE REPAIR UNDER TRIANGULAR RESECTION TECHNIQUE

(71) Applicant: Epygon, Paris (FR)

(72) Inventors: Enrico Pasquino, Savigny (CH); Marcio Scorsin, Curitiba (BR)

(73) Assignee: Epygon, Paris (FR)

( * ) Notice: Subject to any disclaimer, the term of this patent is extended or adjusted under 35 U.S.C. 154(b) by 152 days.

(21) Appl. No.: 15/541,722

(22) PCT Filed: Jan. 8, 2016

(86) PCT No.: PCT/IB2016/050081
§ 371 (c)(1),
(2) Date: Jul. 6, 2017

(87) PCT Pub. No.: WO2016/113649
PCT Pub. Date: Jul. 21, 2016

(65) Prior Publication Data
US 2018/0000473 A1   Jan. 4, 2018

(30) Foreign Application Priority Data

Jan. 12, 2015  (WO) .................. PCT/IB2015/050227
Mar. 30, 2015  (CH) .................................... 00453/15

(51) Int. Cl.
*A61B 17/00* (2006.01)
*A61B 17/072* (2006.01)
(Continued)

(52) U.S. Cl.
CPC ...... *A61B 17/00234* (2013.01); *A61B 17/072* (2013.01); *A61B 17/295* (2013.01);
(Continued)

(58) Field of Classification Search
CPC .... A16B 17/265; A61F 2/2427; A61F 2/2496; A61B 17/0281; A61B 2017/0243;
(Continued)

(56) References Cited

U.S. PATENT DOCUMENTS 5,626,607 A   5/1997  Malecki et al.
6,663,639 B1  12/2003 Laufer et al.
(Continued)

FOREIGN PATENT DOCUMENTS

JP   2003 502098 A   1/2003
JP   2004-041580 A   2/2004
(Continued)

OTHER PUBLICATIONS

Chinese Office Action for Application CN201680005476.1 English translation dated Sep. 26, 2019.
(Continued)

*Primary Examiner* — Martin T Ton
(74) *Attorney, Agent, or Firm* — Andre Roland S.A.; Nikolaus Schibli

(57) ABSTRACT

Medical device for transcatheter heart valve repair comprising a grasping tweezer (1) and a plicating tweezer (2), said grasping tweezer (1) being adapted to grasp a leaflet rim (3) and said plicating tweezer (2) comprising two rotatable flaps (4,5) and a central shaft (6) around which said flaps (4,5) may rotate in a "butterfly manner", in such a way that the plicating tweezer (2) may adopt a closed or an open configuration. The invention also relates to a method for using this medical device.

14 Claims, 36 Drawing Sheets

(51) Int. Cl.
*A61B 17/295* (2006.01)
*A61B 17/29* (2006.01)

(52) U.S. Cl.
CPC .............. *A61B 2017/00243* (2013.01); *A61B 2017/00287* (2013.01); *A61B 2017/00783* (2013.01); *A61B 2017/07214* (2013.01); *A61B 2017/2908* (2013.01); *A61B 2017/2927* (2013.01)

(58) Field of Classification Search
CPC .. A61B 2017/0225; A61B 2017/07214; A61B 2017/1225; A61B 2017/2906; A61B 2017/2926
See application file for complete search history.

(56) References Cited

U.S. PATENT DOCUMENTS

| | | | |
|---|---|---|---|
| 7,235,089 | B1* | 6/2007 | McGuckin, Jr. ............................ A61B 17/00234 227/180.1 |
| 2002/0193816 | A1 | 12/2002 | Laufer et al. |
| 2005/0251177 | A1 | 11/2005 | Saadat et al. |
| 2005/0267529 | A1 | 12/2005 | Crockett et al. |
| 2007/0167960 | A1 | 7/2007 | Roth et al. |
| 2007/0185513 | A1* | 8/2007 | Woolfson ......... A61B 17/32002 606/108 |
| 2007/0197858 | A1 | 8/2007 | Goldfarb et al. |
| 2008/0294179 | A1* | 11/2008 | Balbierz ............ A61B 17/0643 606/151 |
| 2008/0319455 | A1 | 12/2008 | Harris et al. |
| 2009/0105814 | A1 | 4/2009 | Groothuis et al. |
| 2009/0198254 | A1 | 8/2009 | Laufer et al. |
| 2009/0312602 | A1 | 12/2009 | Sakamoto et al. |
| 2009/0318936 | A1 | 12/2009 | Harris et al. |
| 2013/0116715 | A1 | 5/2013 | Weber |
| 2014/0039511 | A1 | 2/2014 | Morris et al. |
| 2014/0214063 | A1 | 7/2014 | Miyamoto et al. |
| 2014/0214152 | A1 | 7/2014 | Bielefeld |
| 2015/0150620 | A1 | 6/2015 | Miyamoto et al. |
| 2015/0150634 | A1* | 6/2015 | Isoda .................... A61B 17/29 606/130 |

FOREIGN PATENT DOCUMENTS

| | | |
|---|---|---|
| JP | 2007-029195 A | 2/2007 |
| JP | 2008-504904 A | 2/2008 |
| JP | 2008-514307 A | 5/2008 |
| WO | WO2006007576 | 1/2006 |
| WO | WO2007067556 A2 | 6/2007 |
| WO | WO 2014/080862 A | 5/2014 |

OTHER PUBLICATIONS

Communication pursuant to article 94(3) for Application EP16708203.1 dated Aug. 28, 2019.
Communication pursuant to article 94(3) for Application EP16708203.1 dated Jan. 4, 2019.
EN translation of Abstract corr to: JP 2004-041580 only avaiable in Japanese.
International Preliminary report on Patantability for PCTIB2016050081 dated Jul. 27, 2017.
International Search Report for PCTIB2016050081 dated May 2, 2016.
Japanese Ofice Action for Application JP 2017-536789 dated Oct. 23, 2019.
Written Opinion of the International Searching Authority for PCTIB2016050081 dated May 2, 2016.

* cited by examiner

Fig. 5 a01
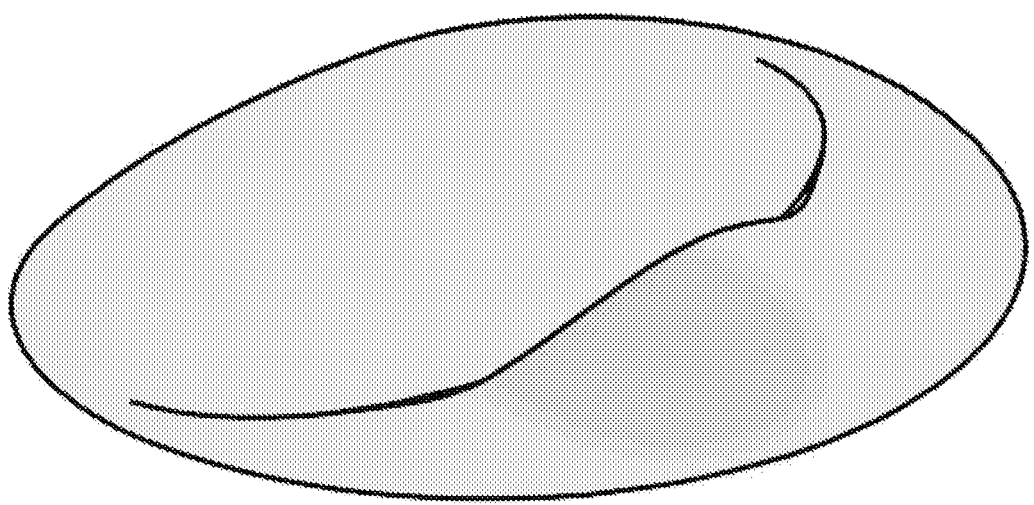

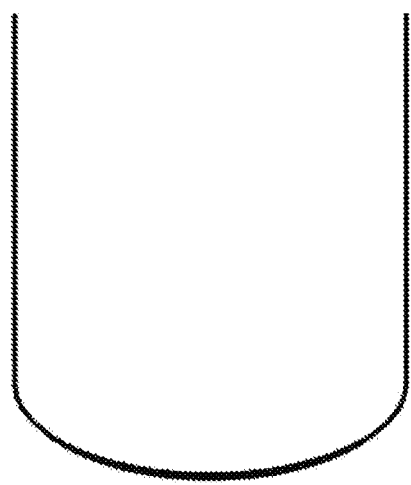
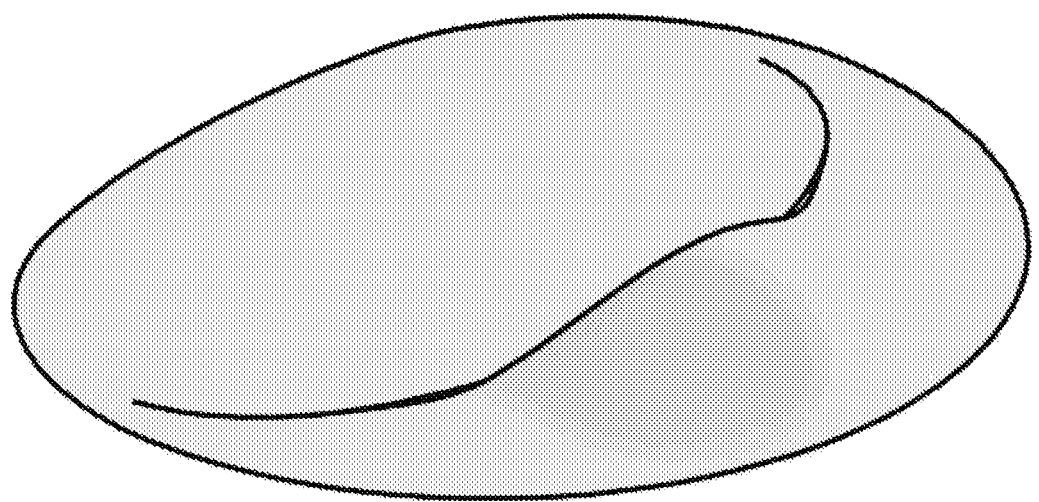
Fig. 5 a02

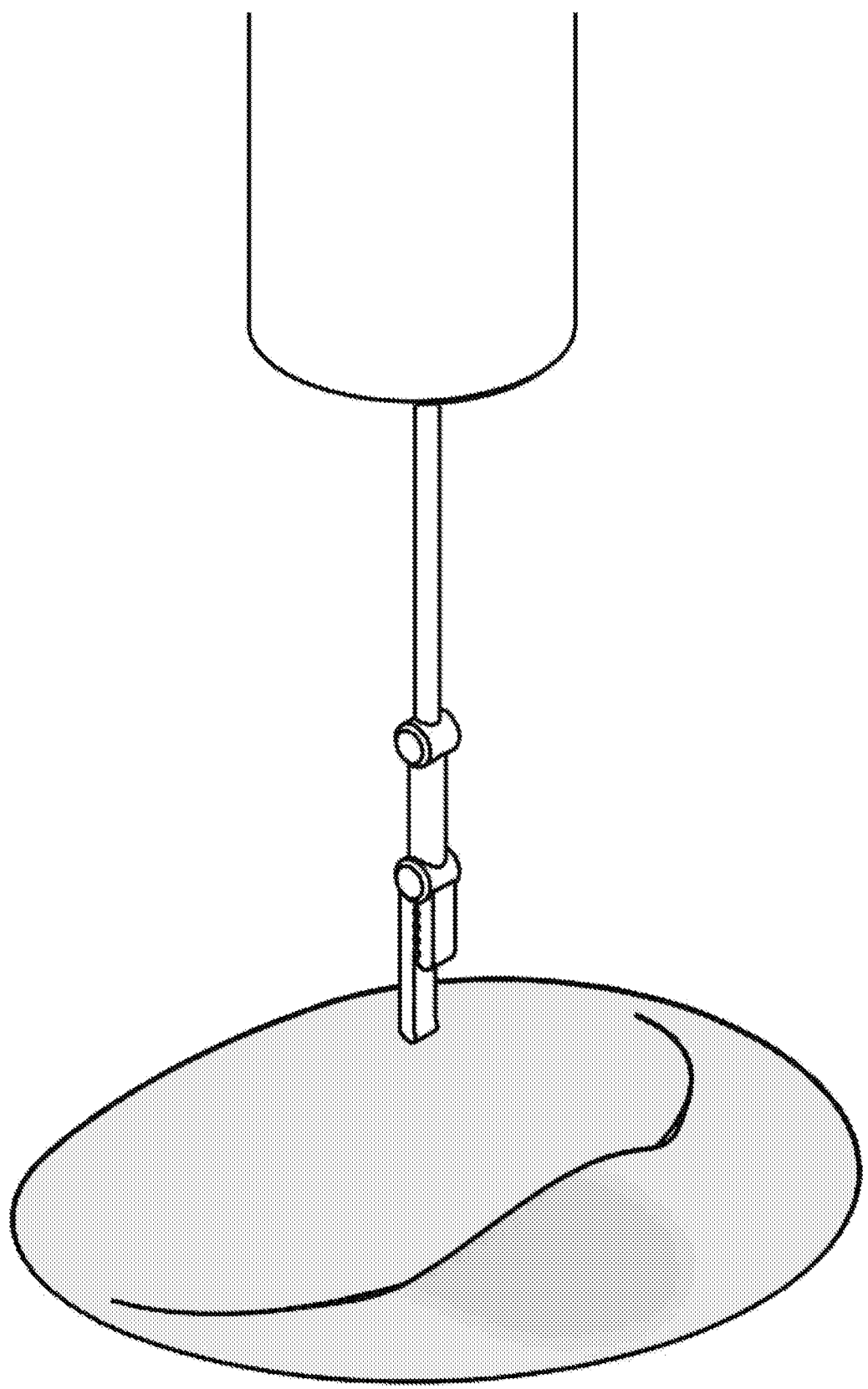
Fig. 5 a03

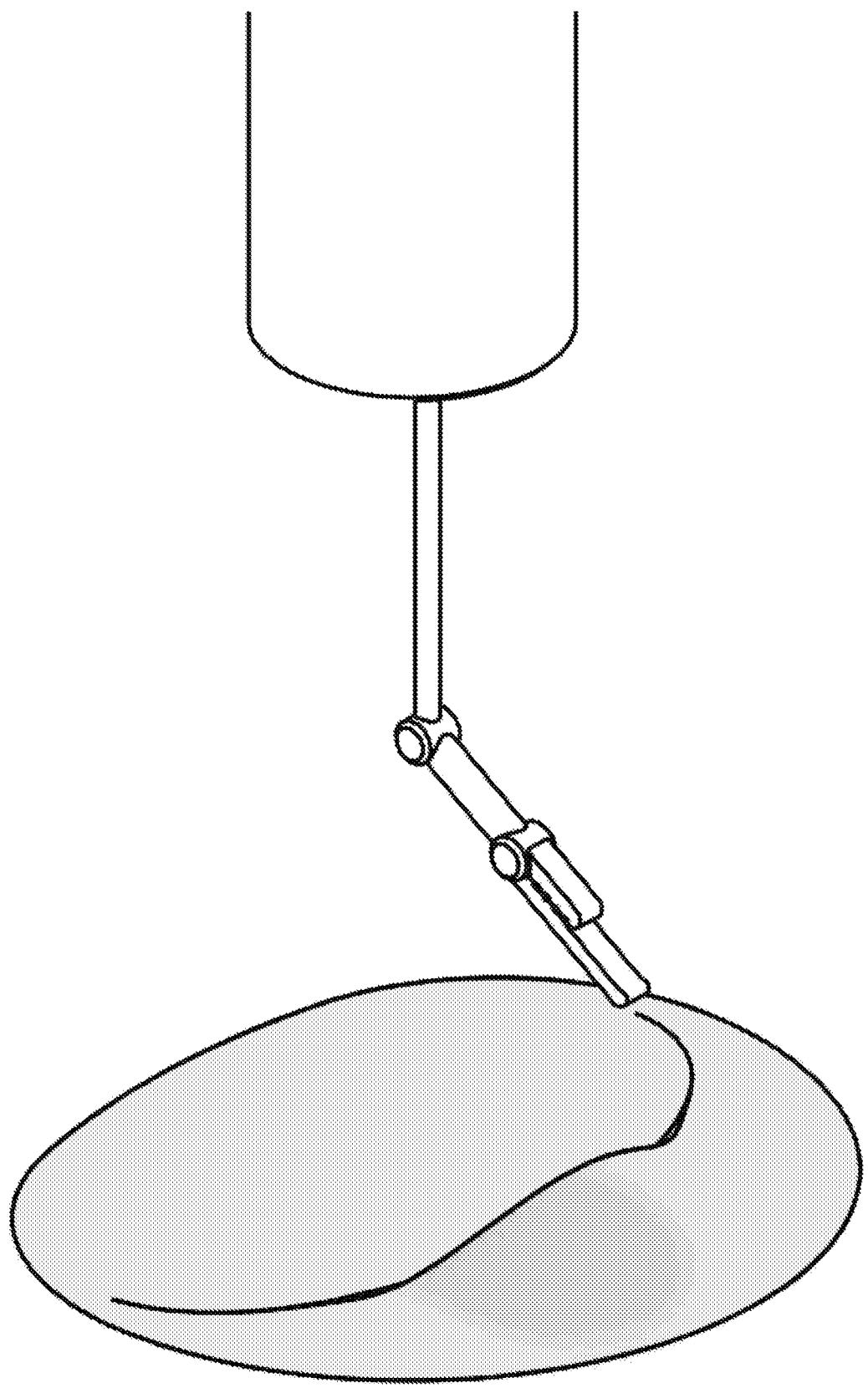
Fig. 5 a04

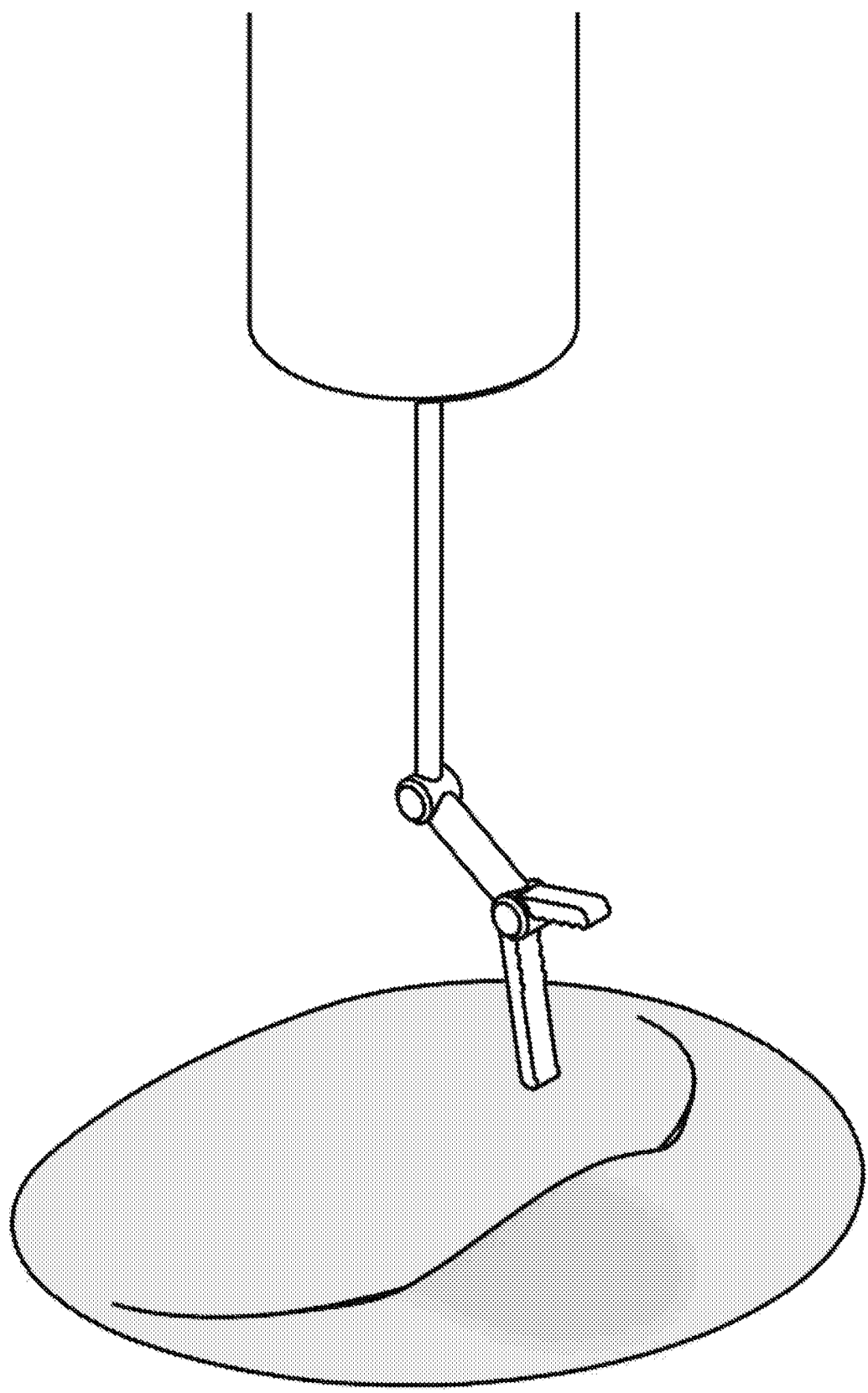
Fig. 5 a05

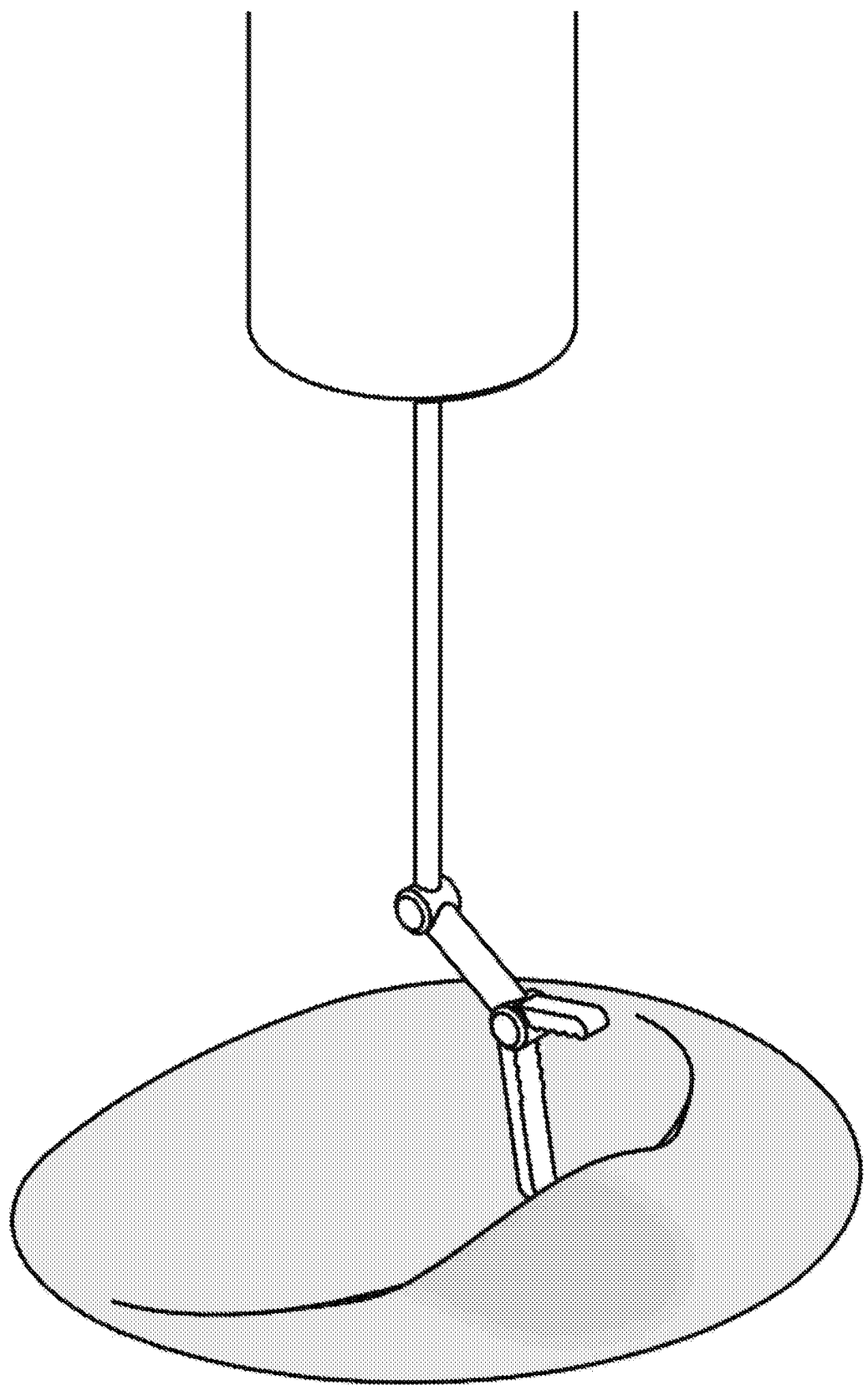
Fig. 5 a06

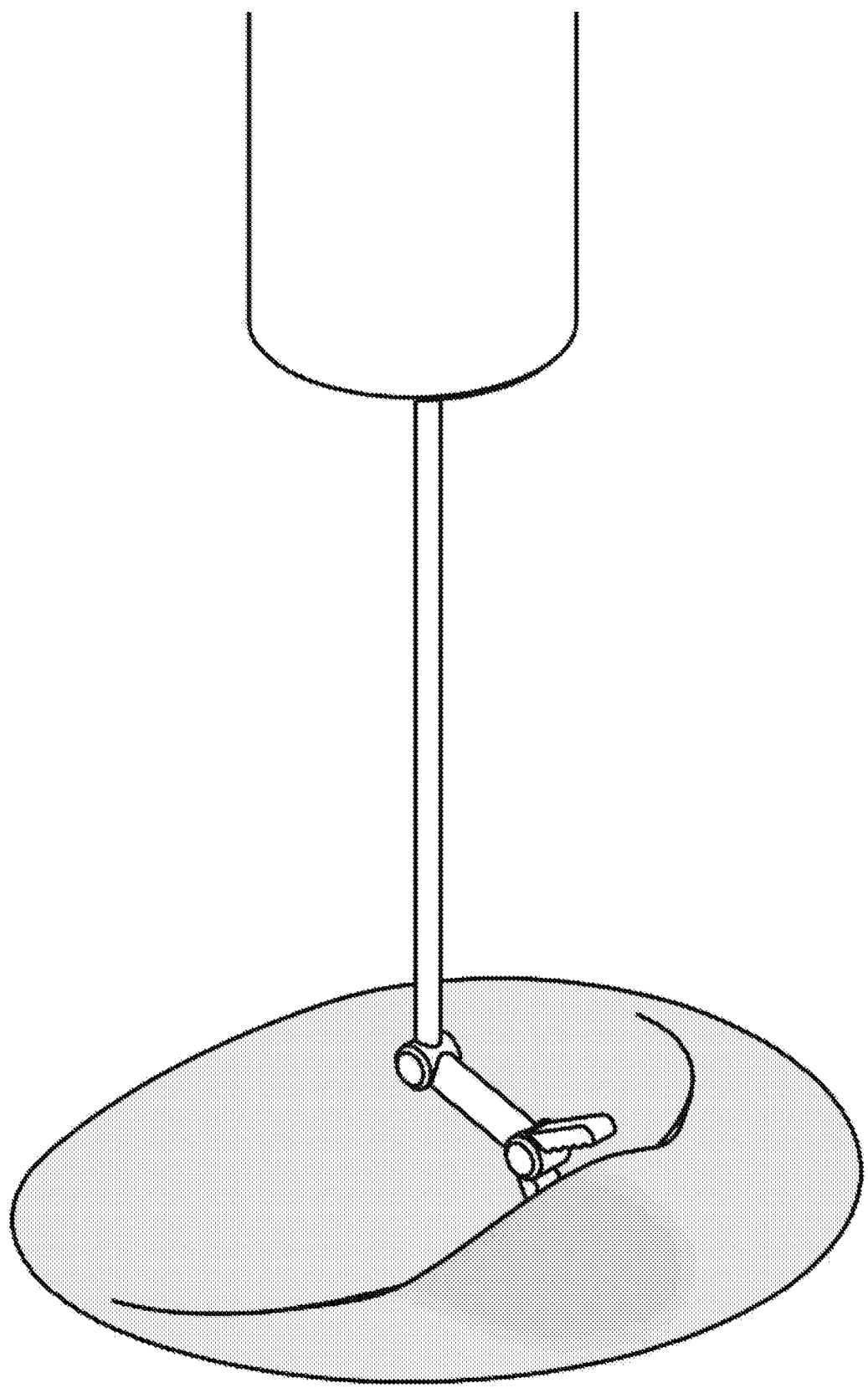
Fig. 5 a07

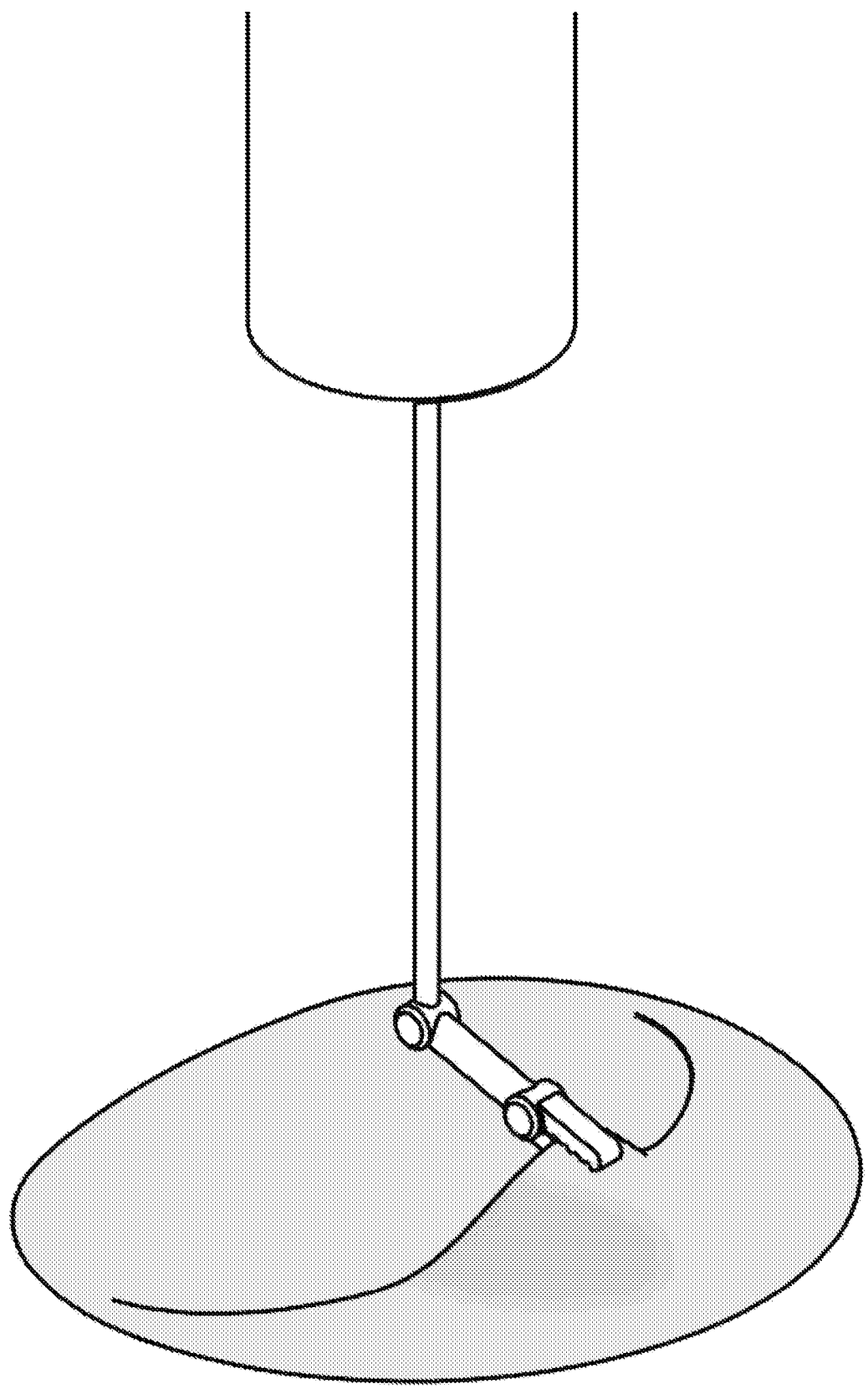
Fig. 5 a08

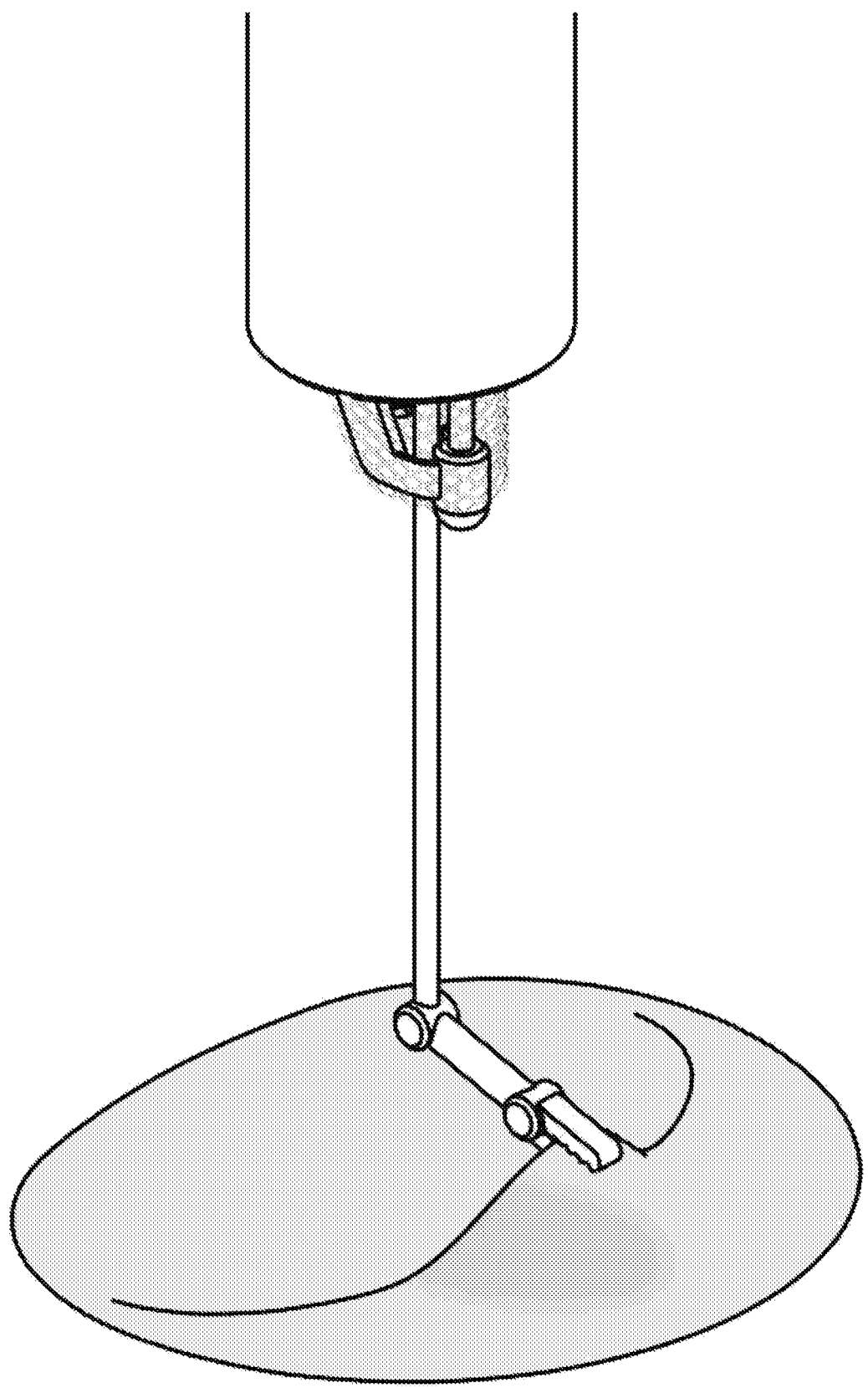
Fig. 5 a09

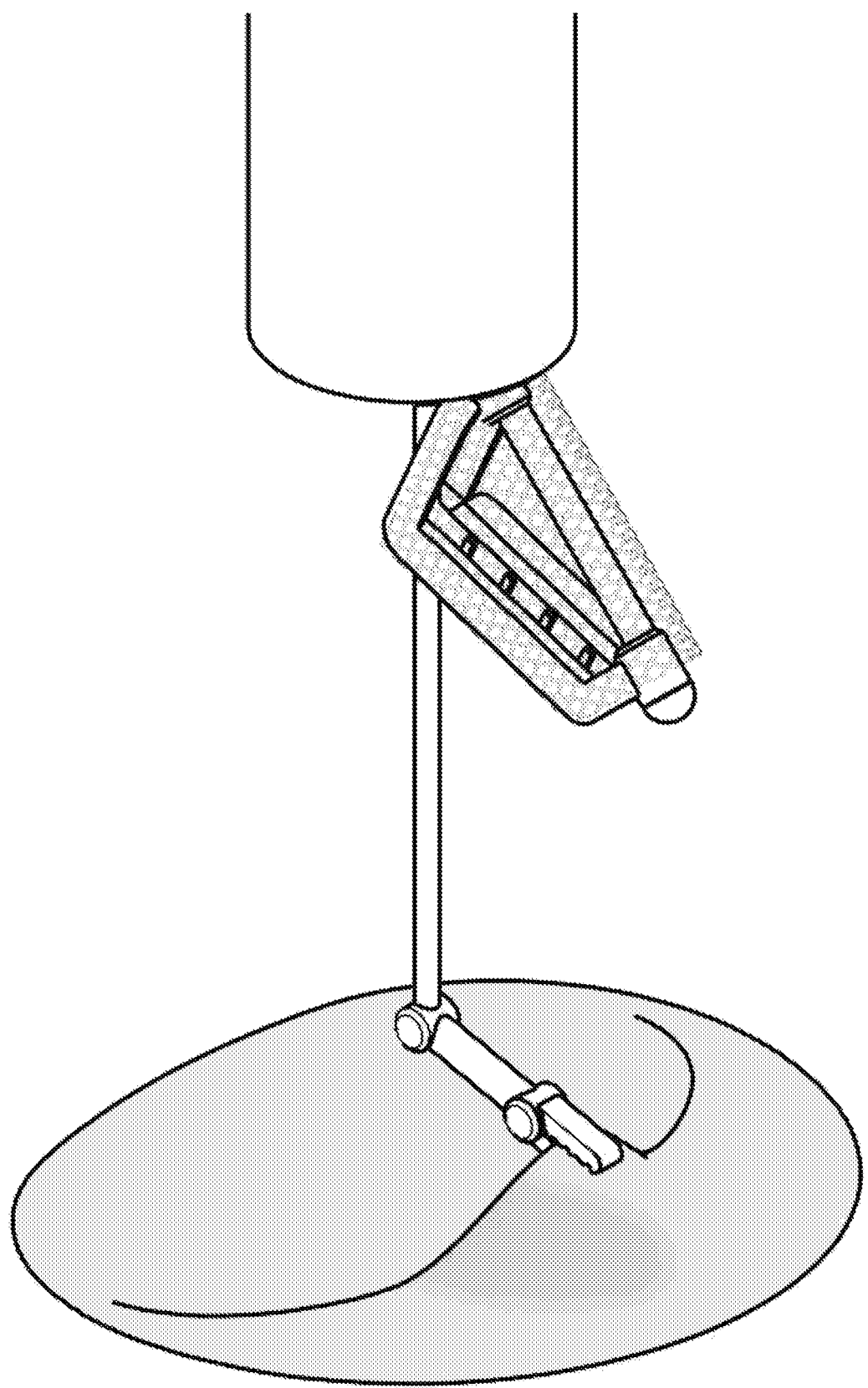
Fig. 5 a10

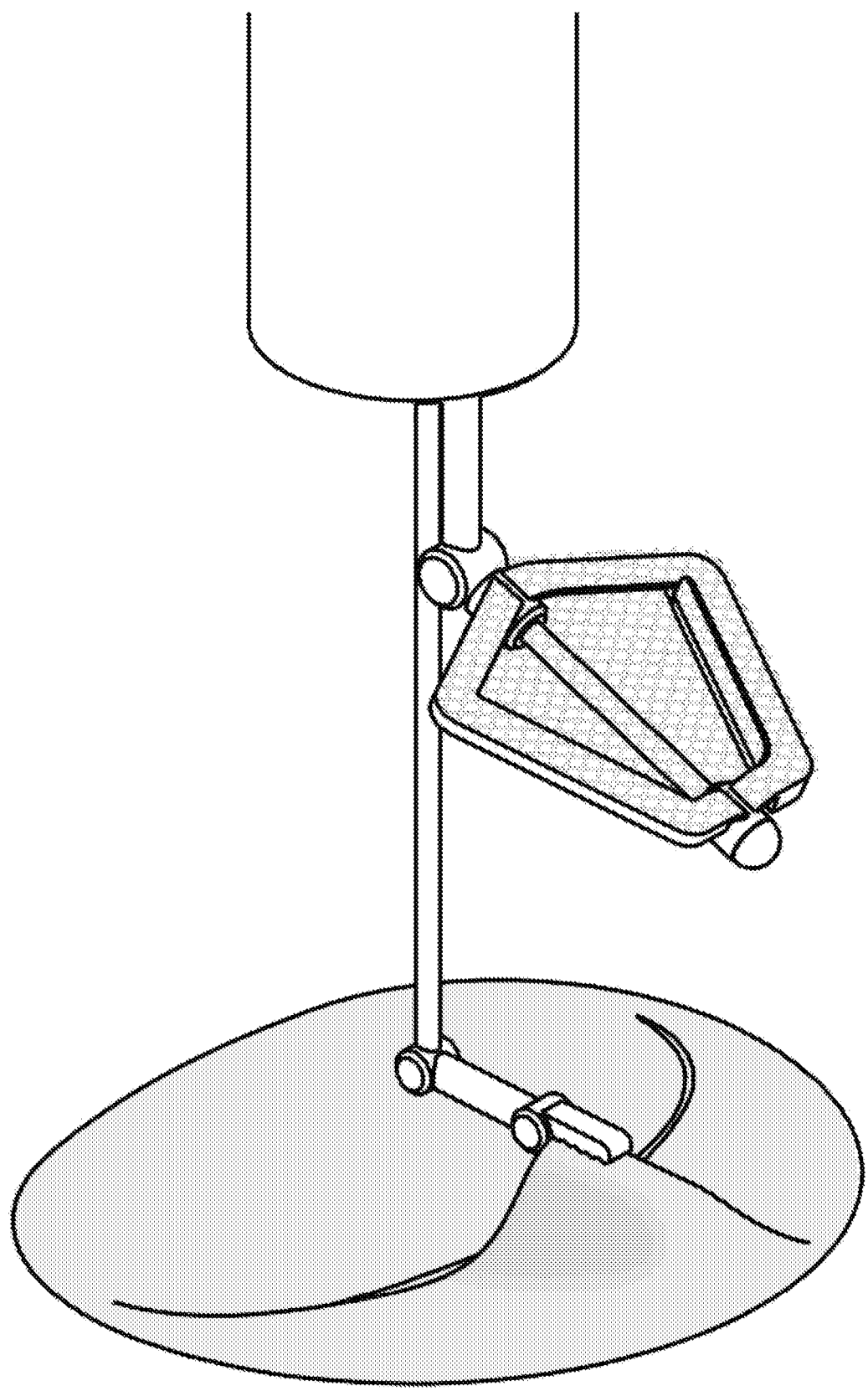
Fig. 5 a11

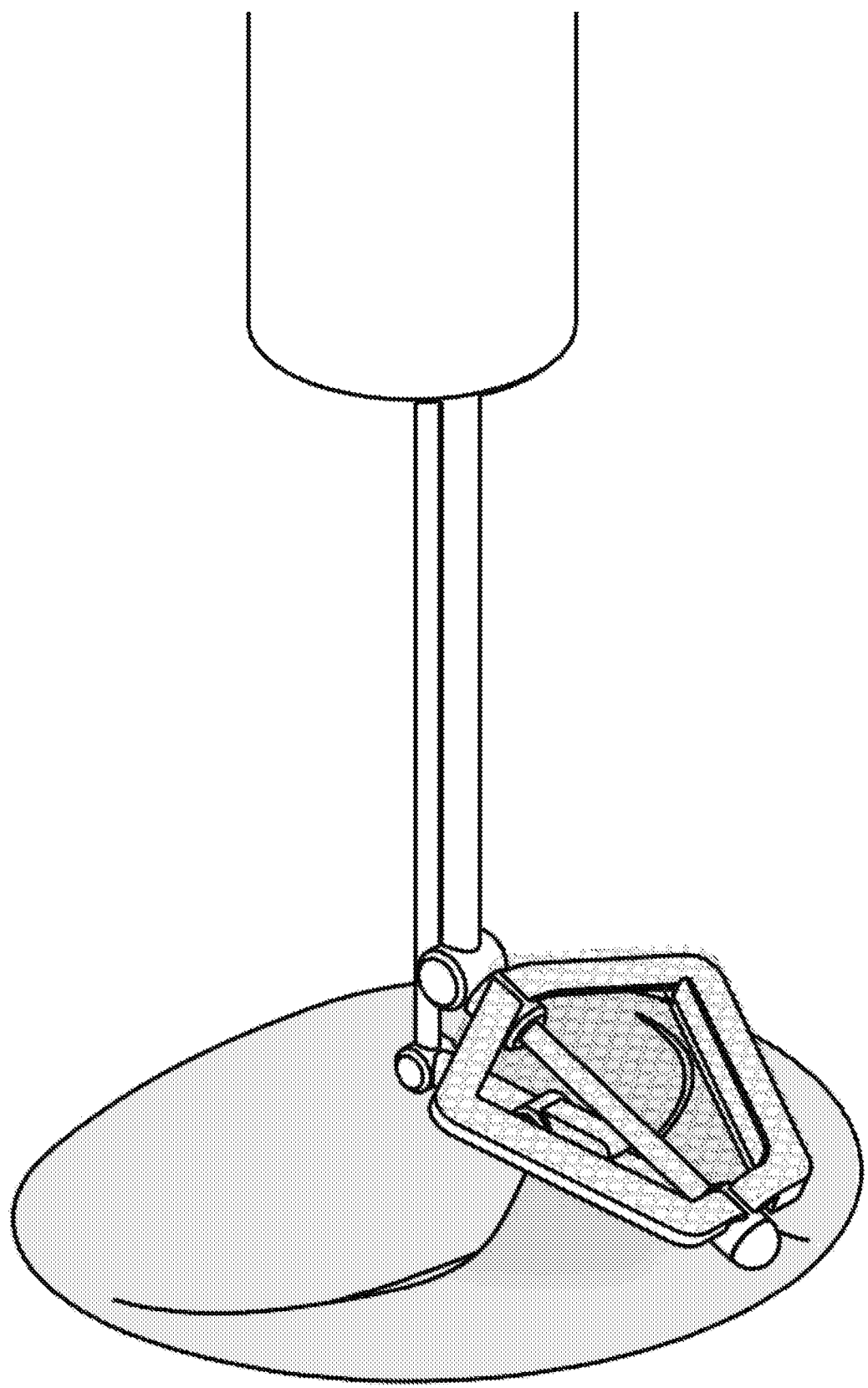
Fig. 5 a12

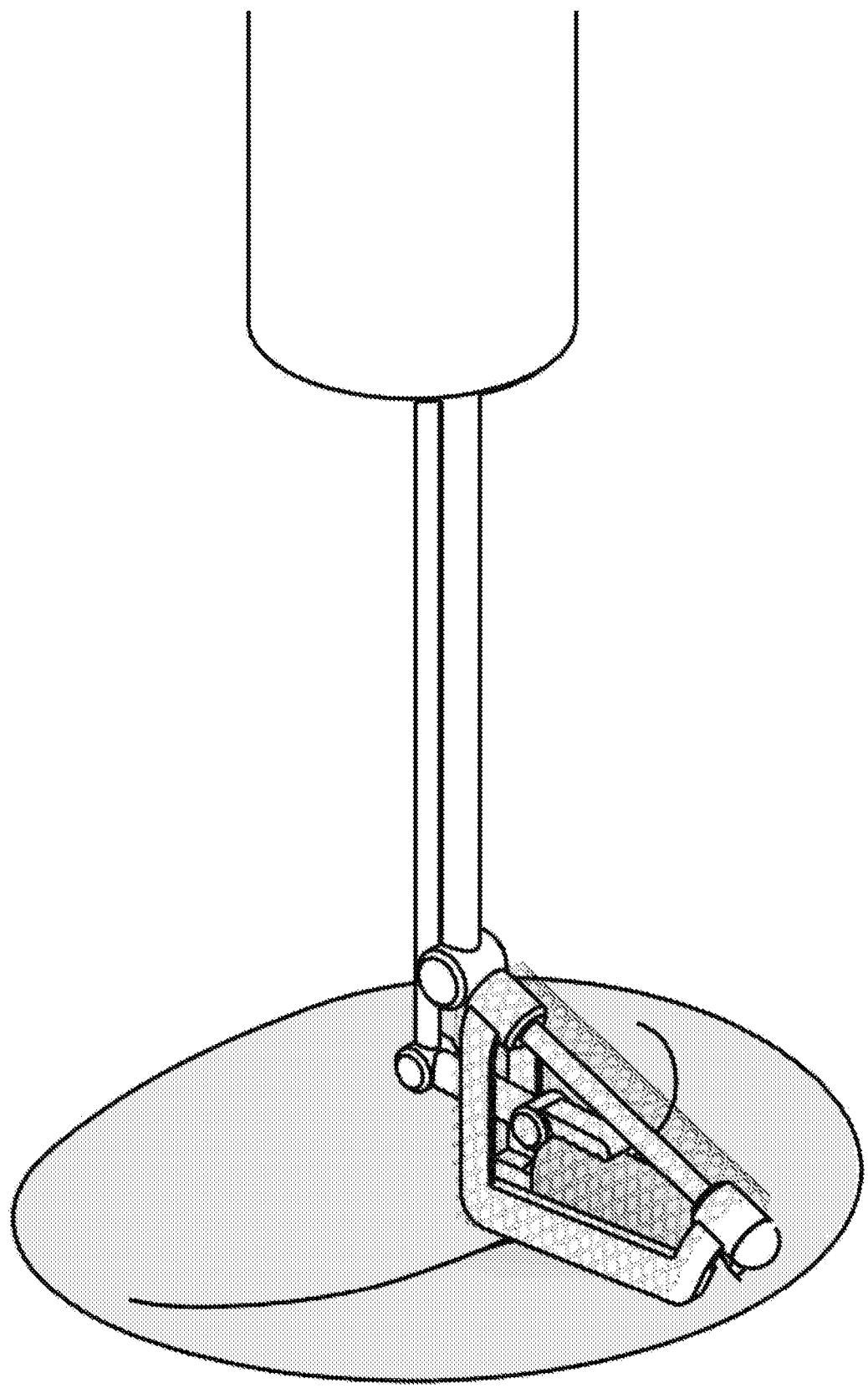
Fig. 5 a13

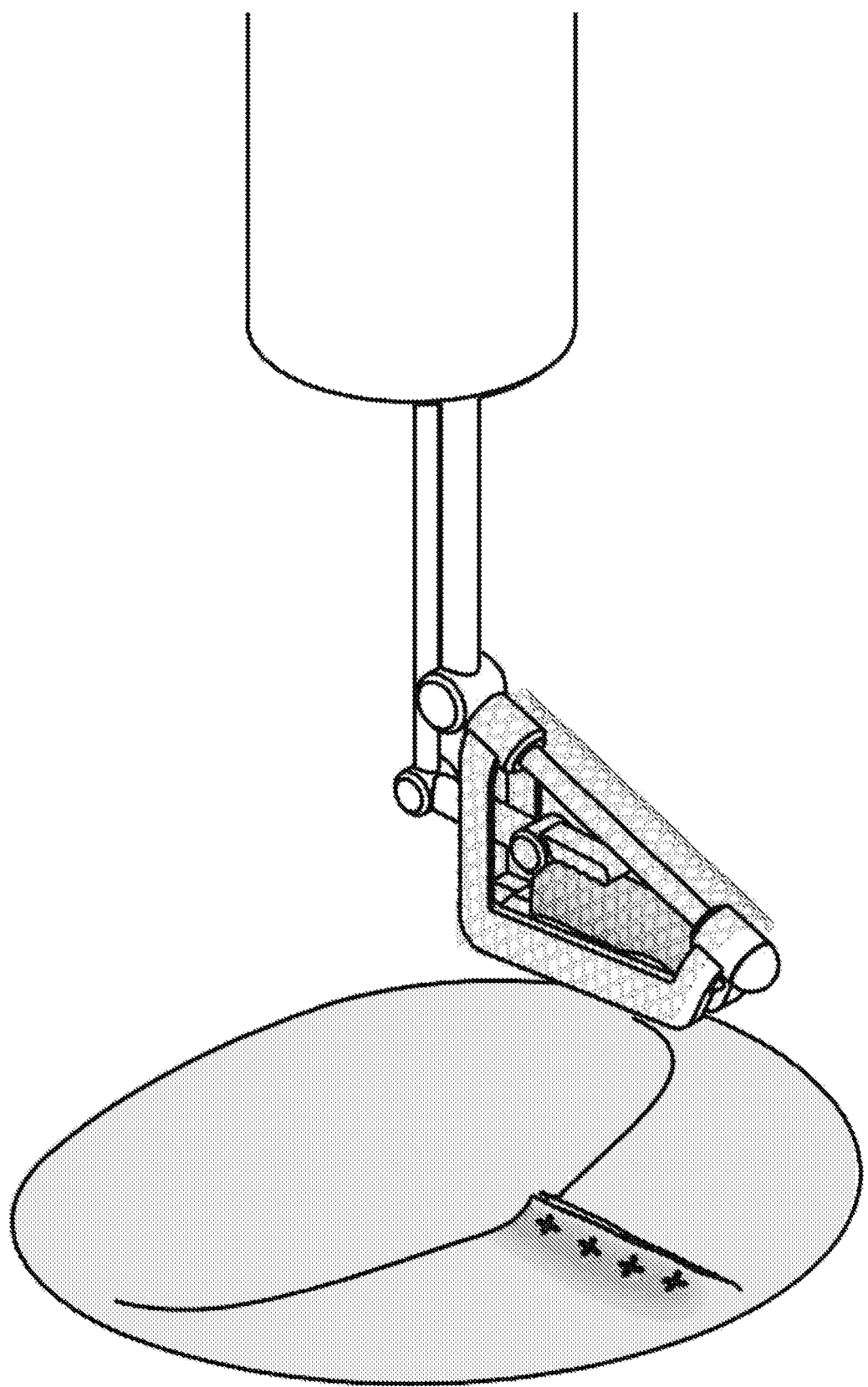
Fig. 5 a14

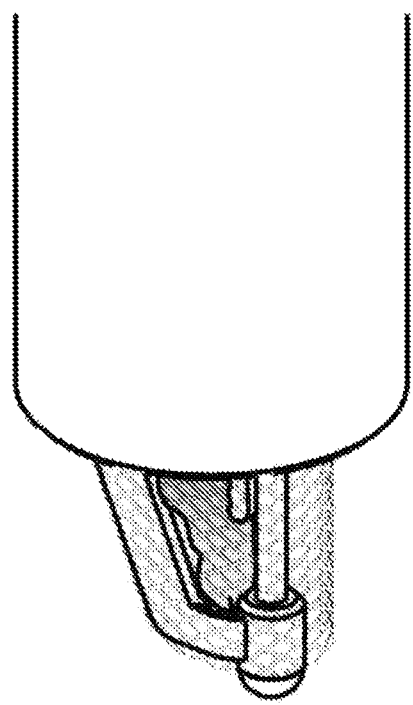
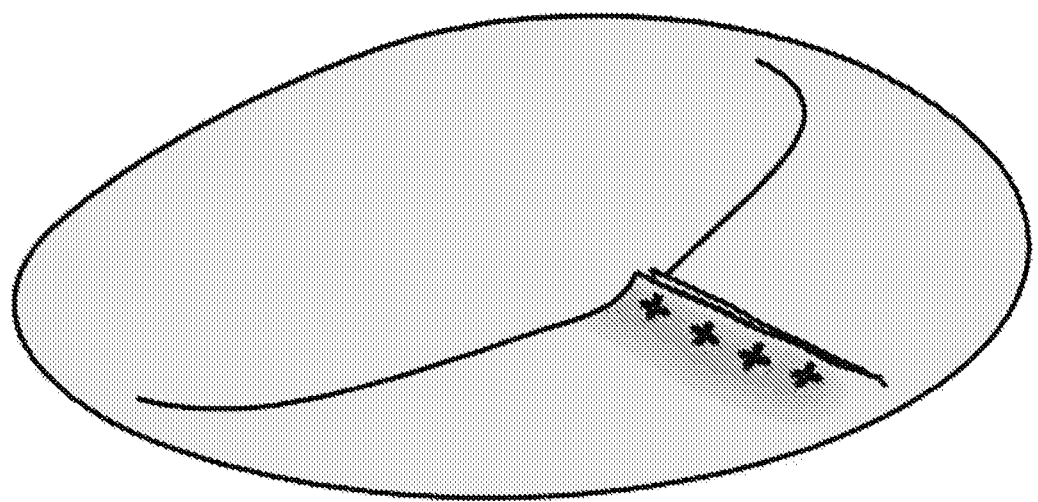
Fig. 5 a15

Fig. 5 a16
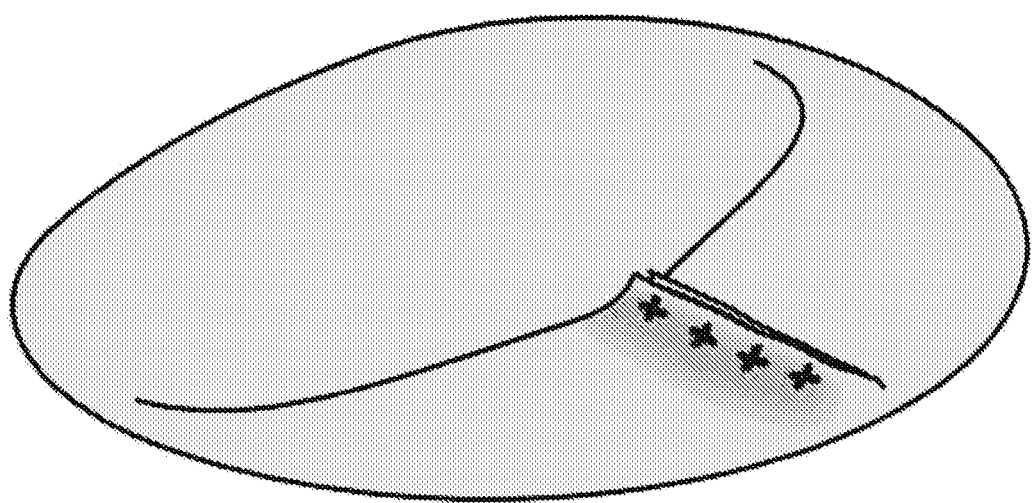

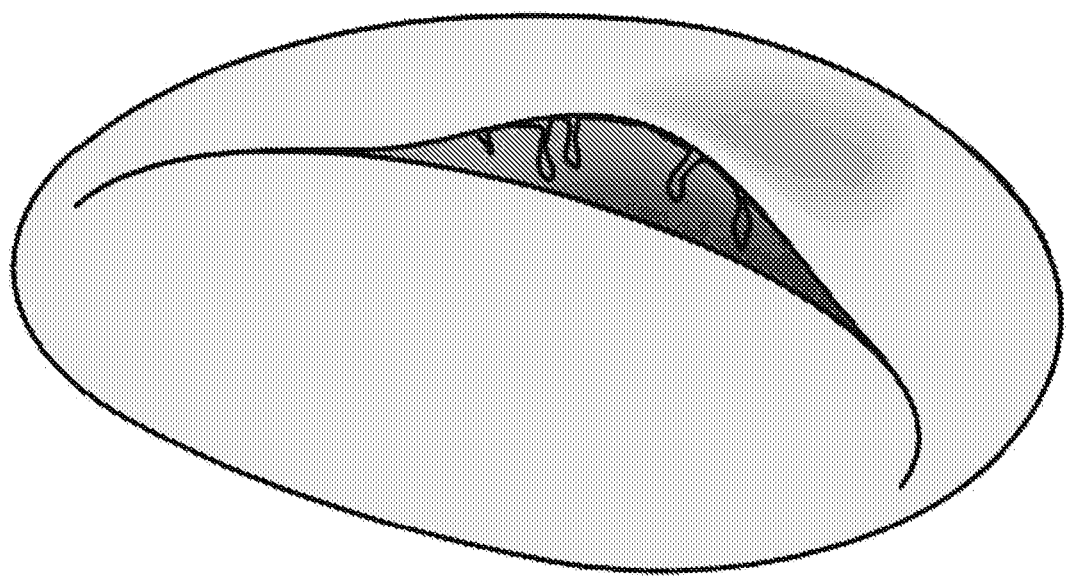
Fig. 5 b01

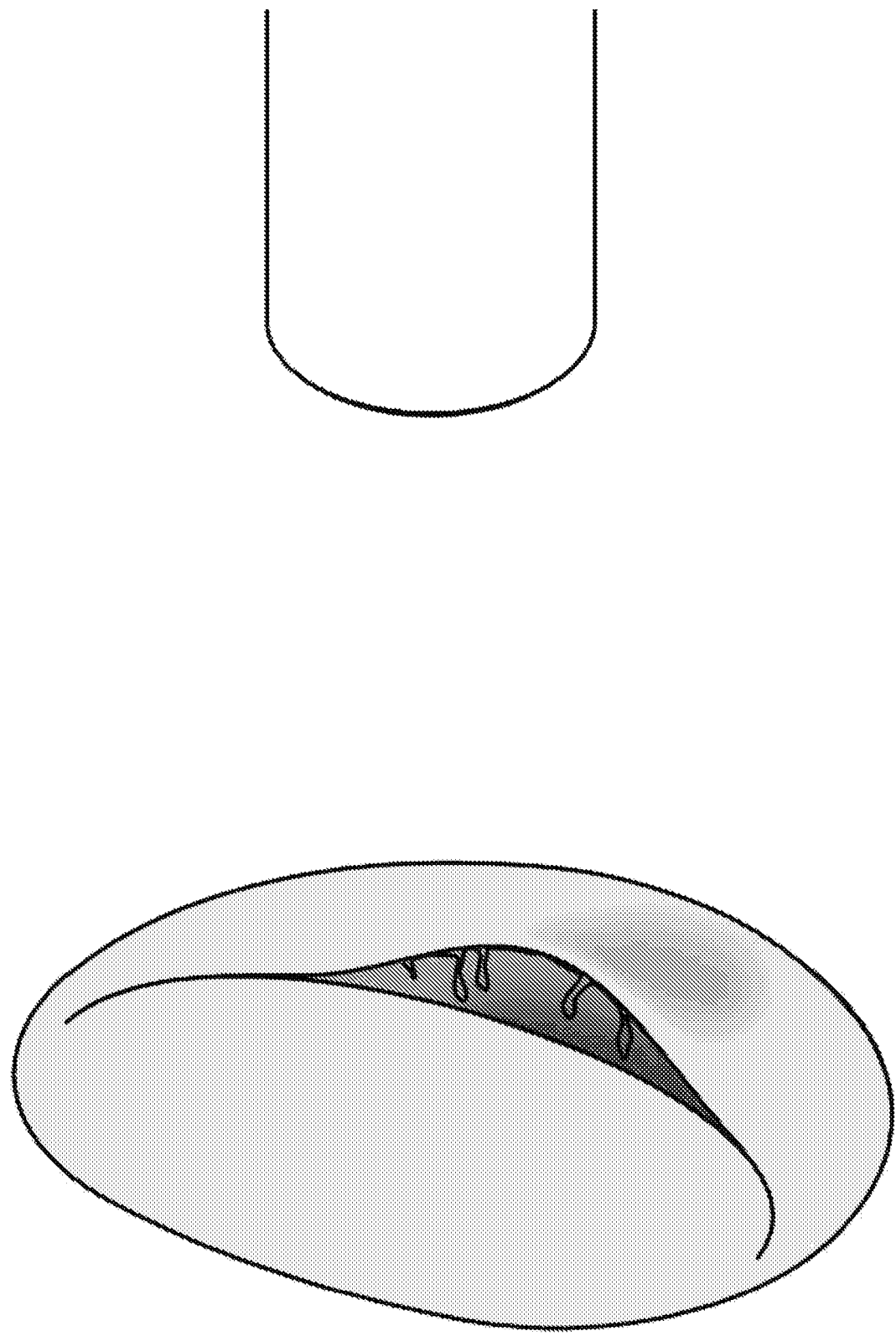
Fig. 5 b02

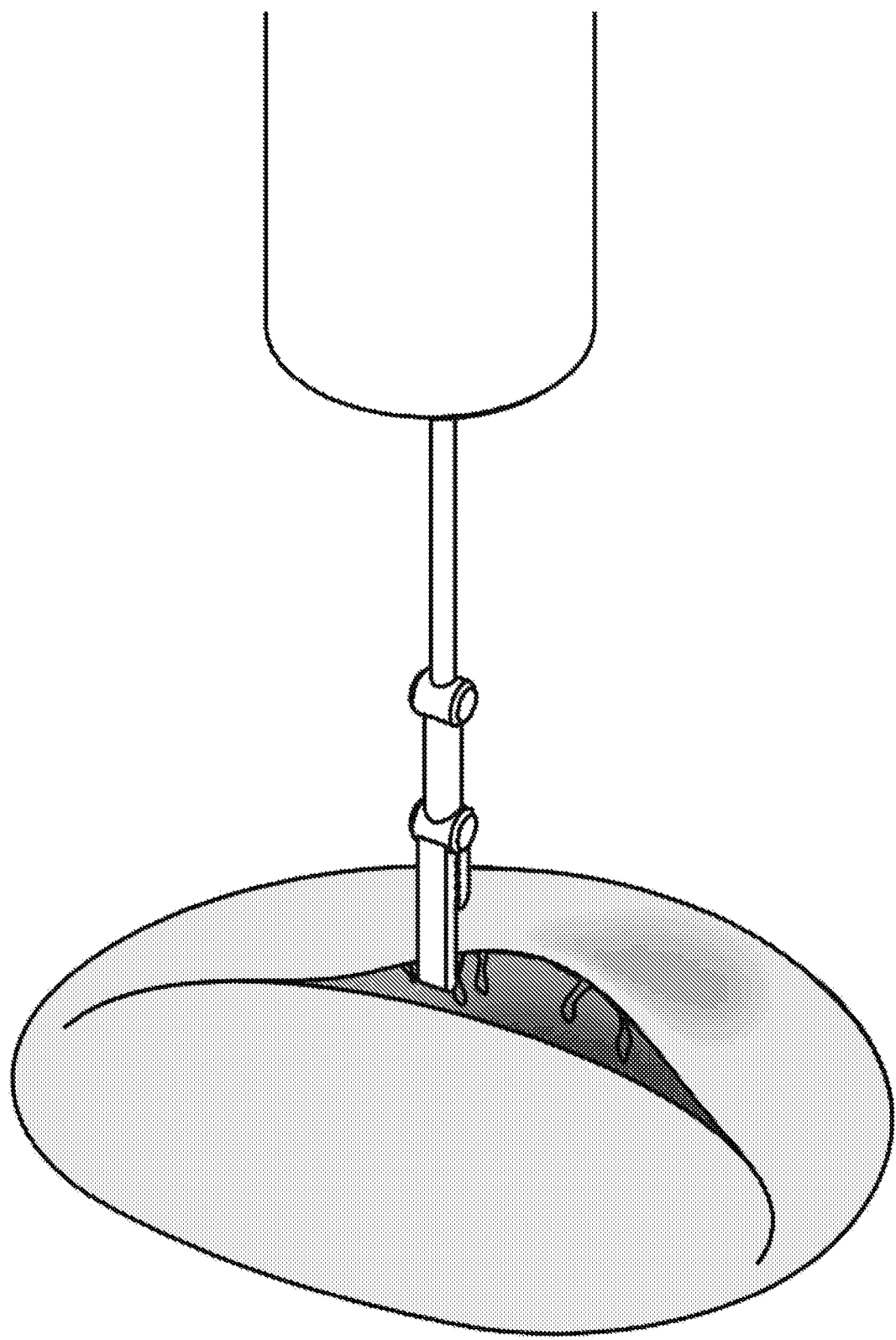
Fig. 5 b03

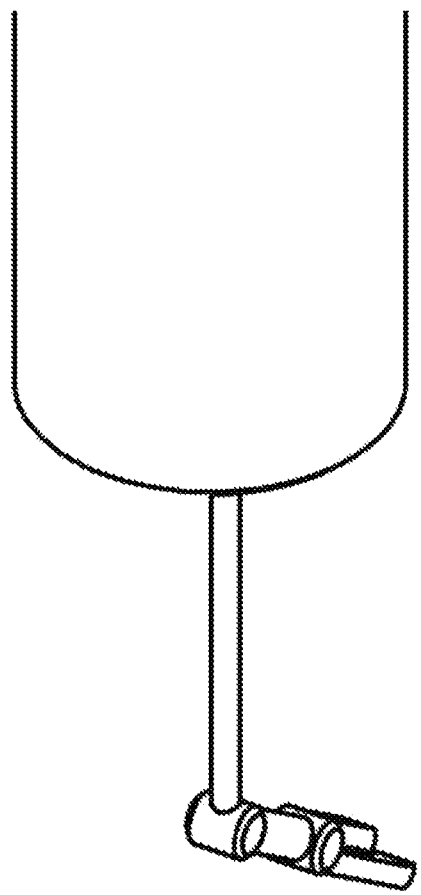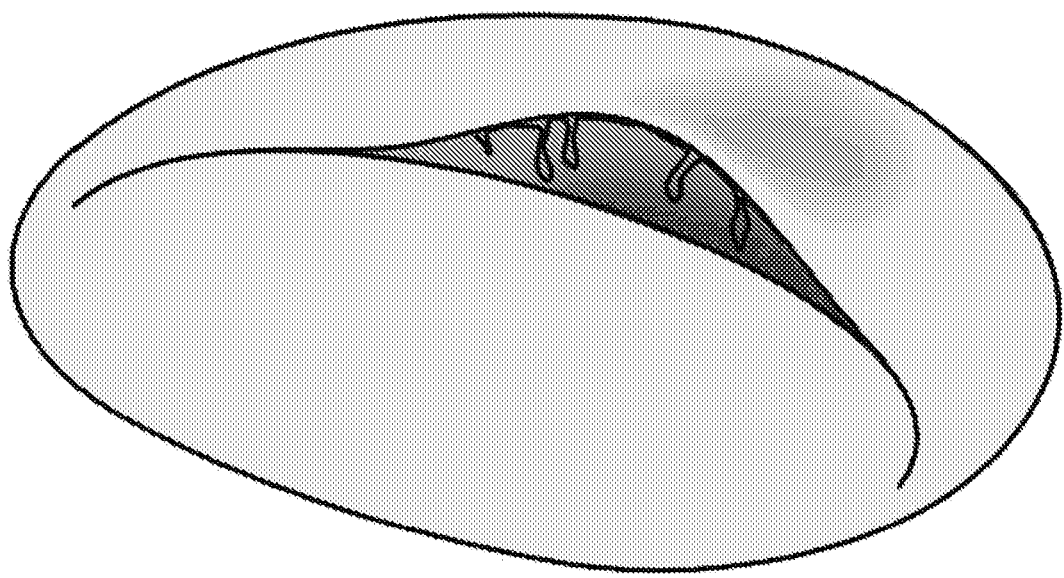
Fig. 5 b04

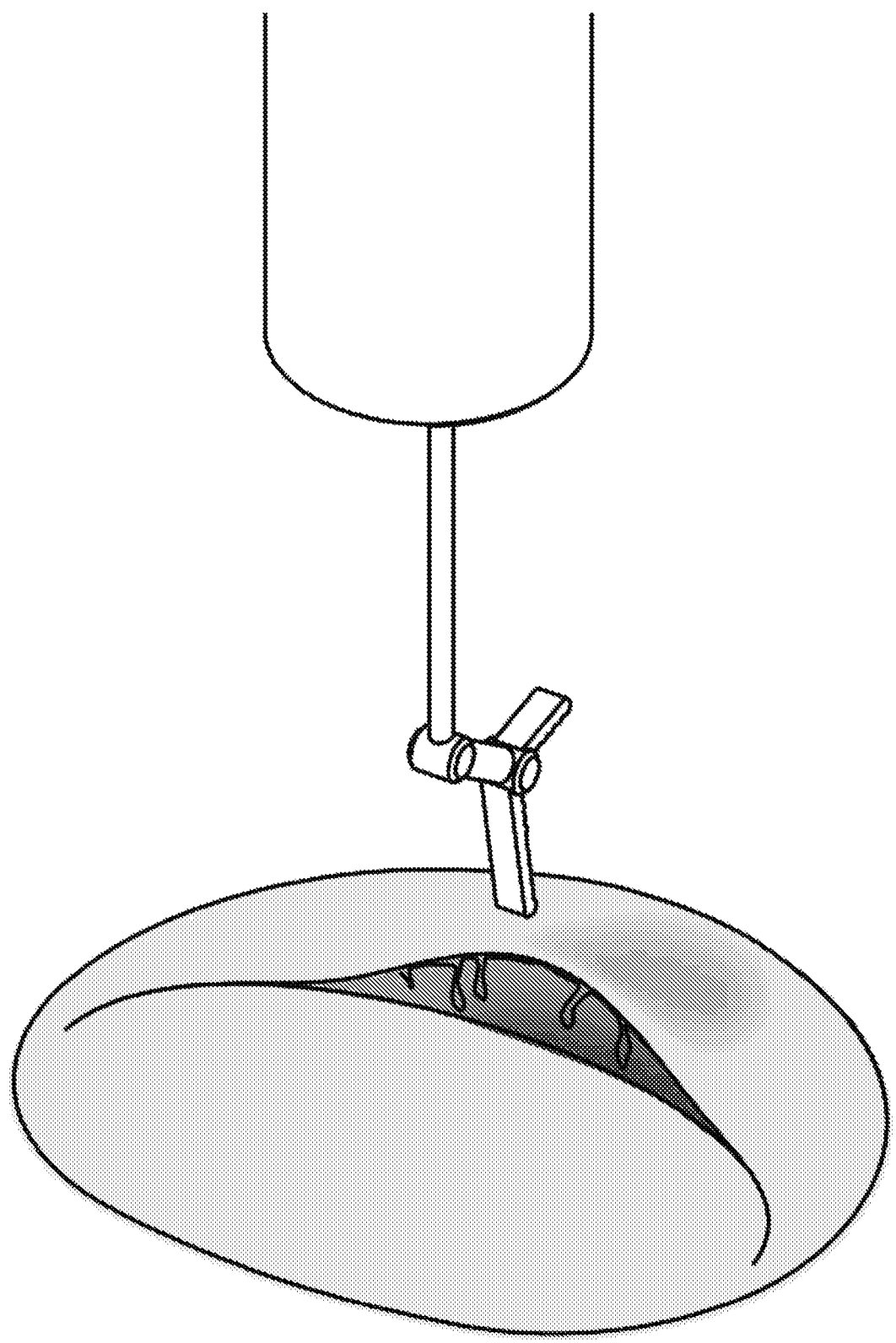
Fig. 5 b05

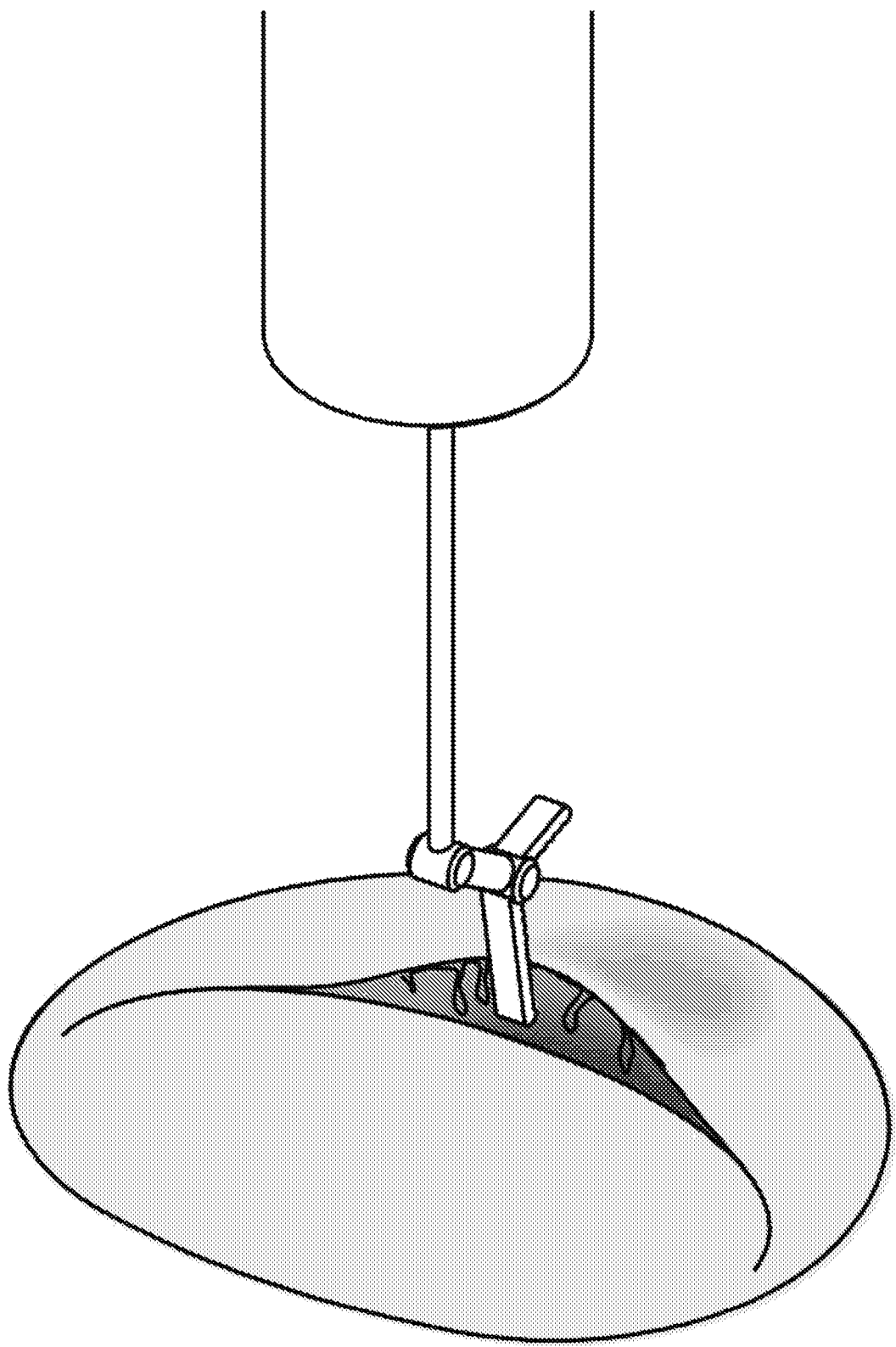
Fig. 5 b06

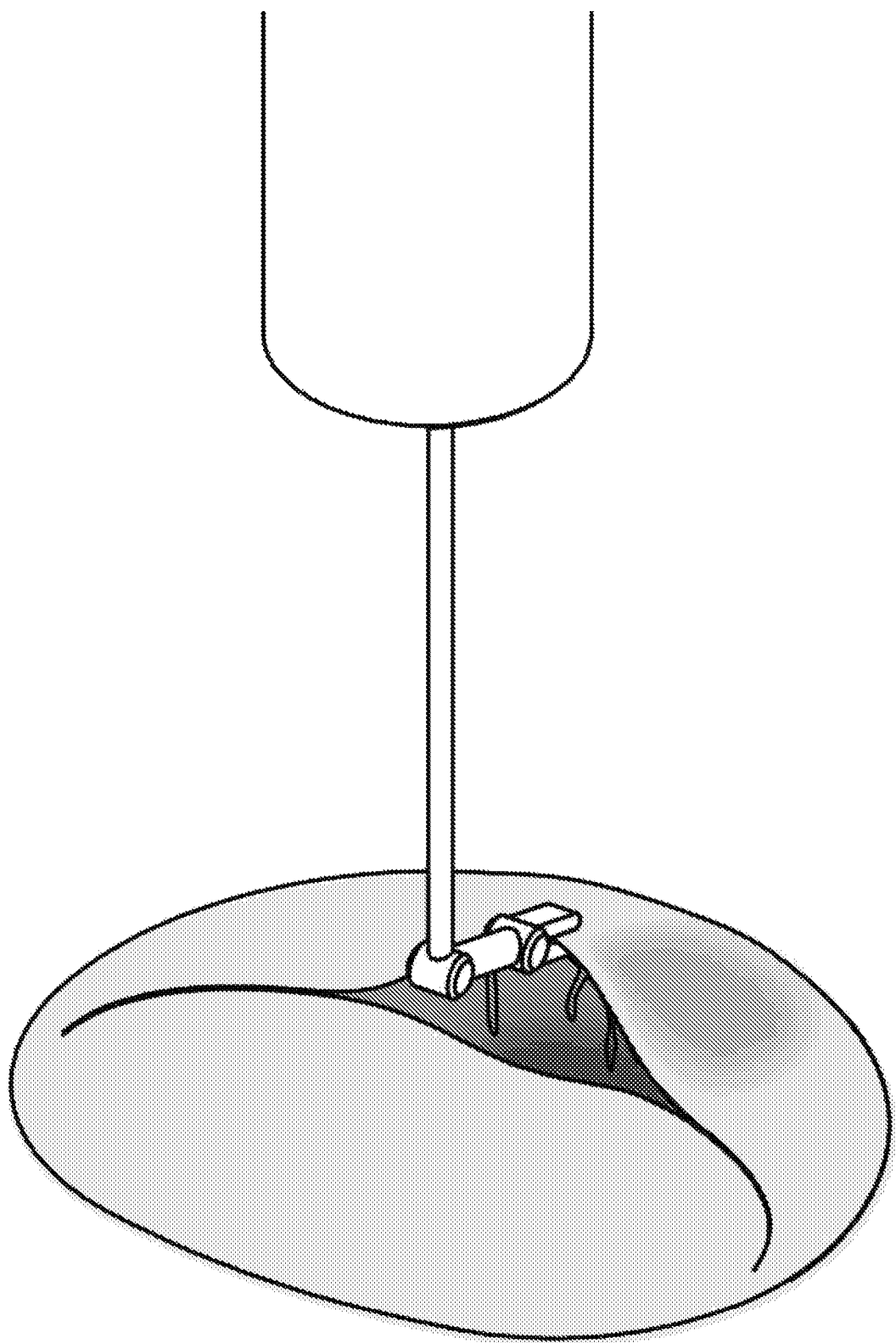
Fig. 5 b07

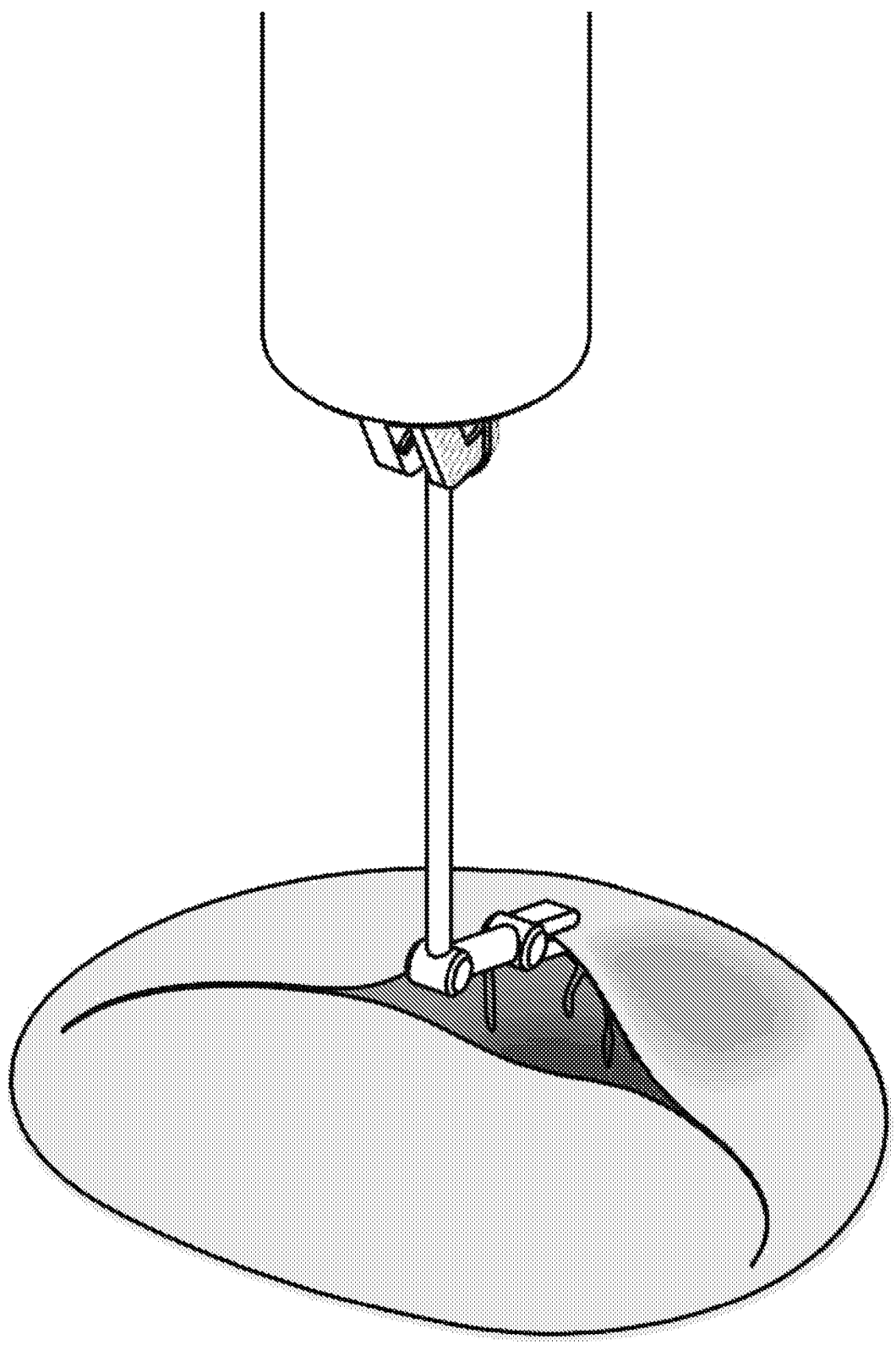
Fig. 5 b08

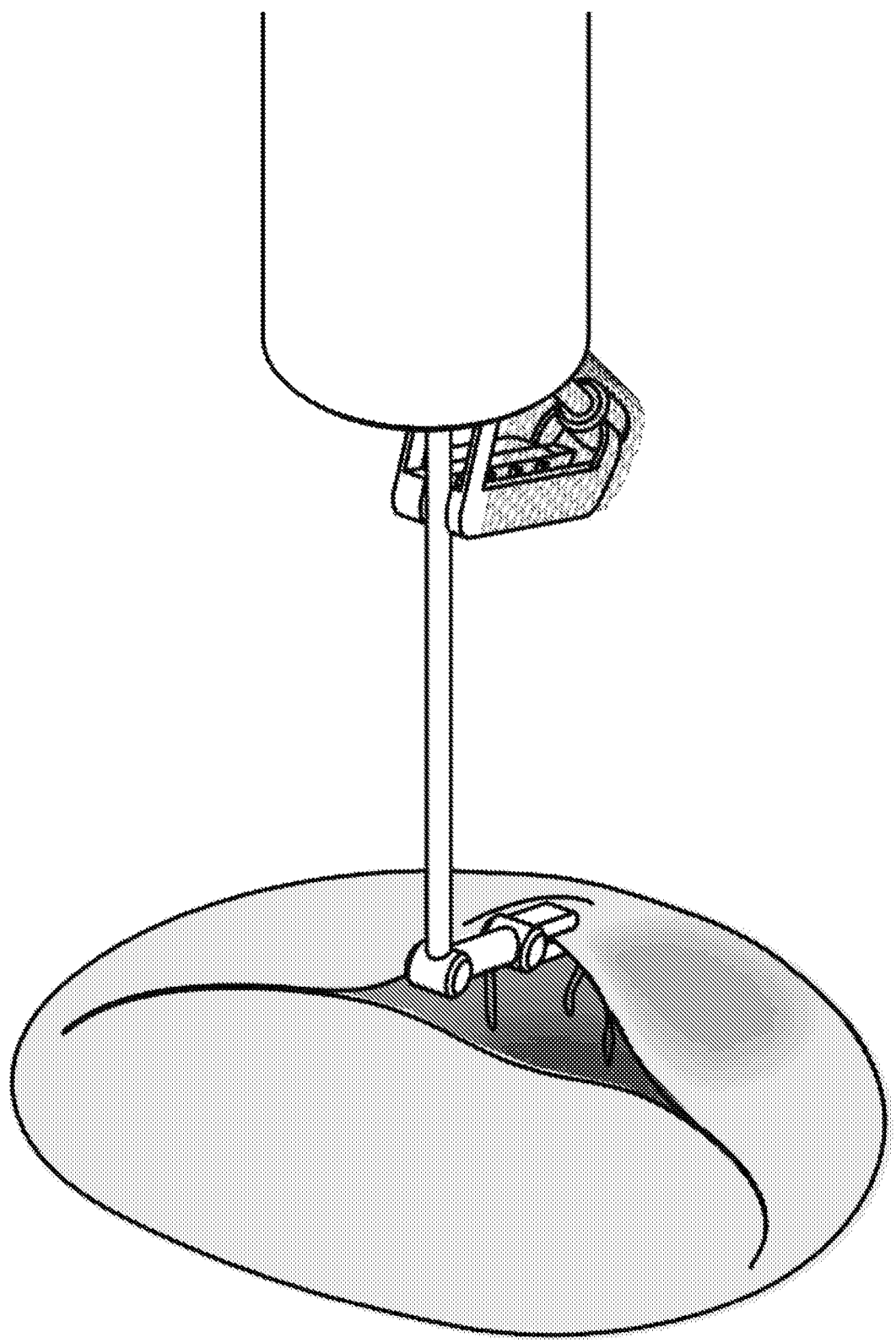
Fig. 5 b09

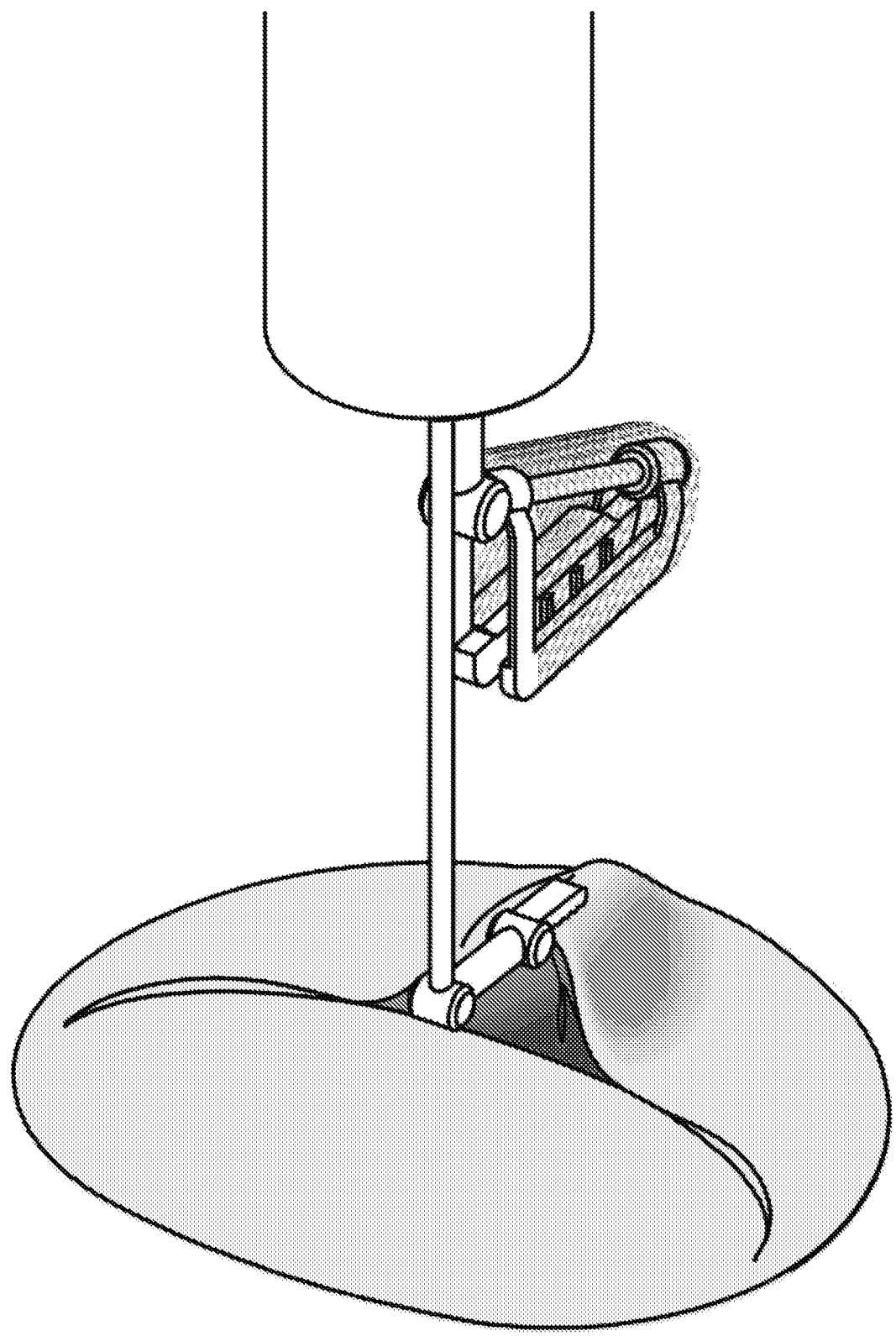
Fig. 5 b10

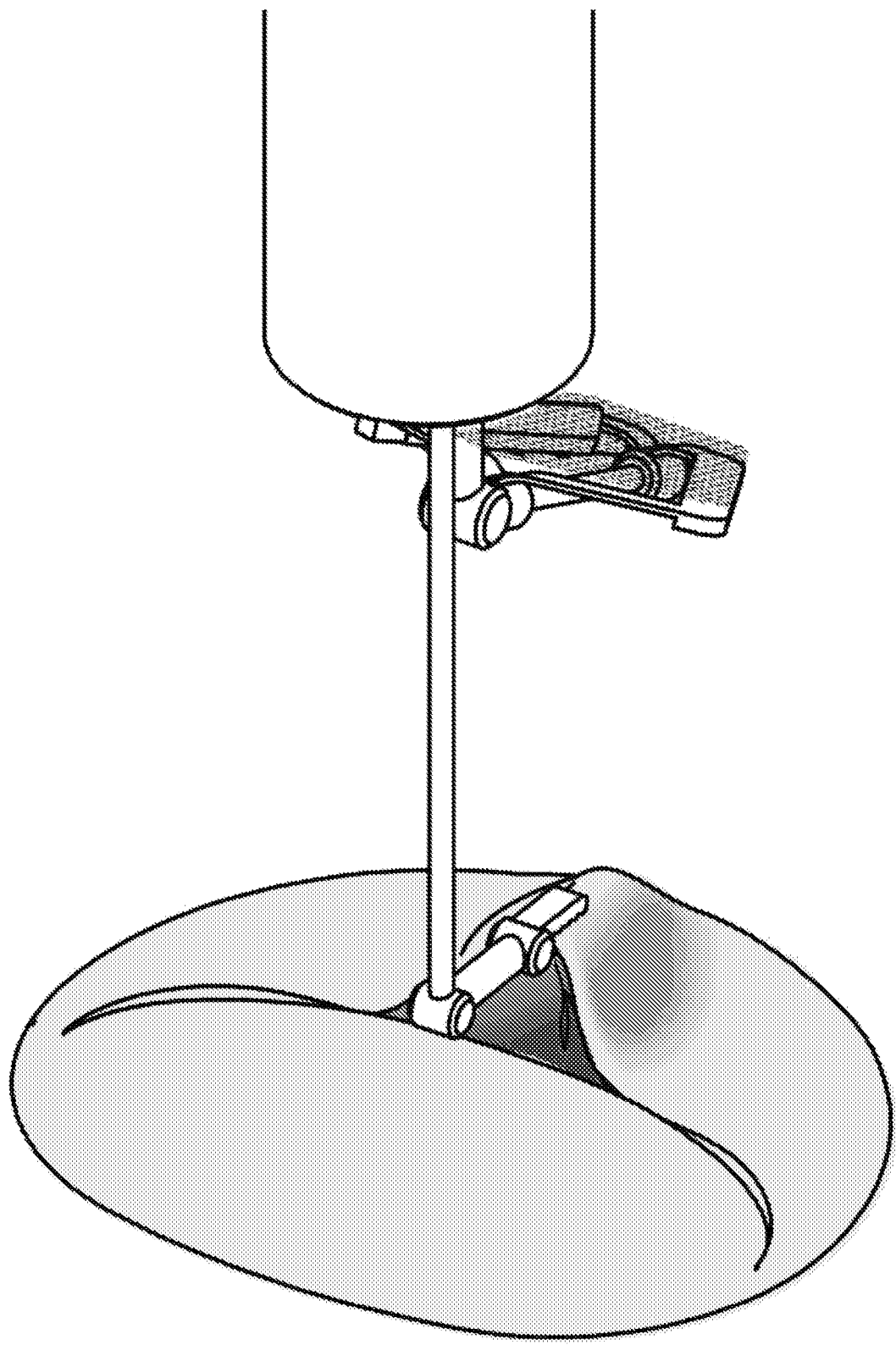
Fig. 5 b11

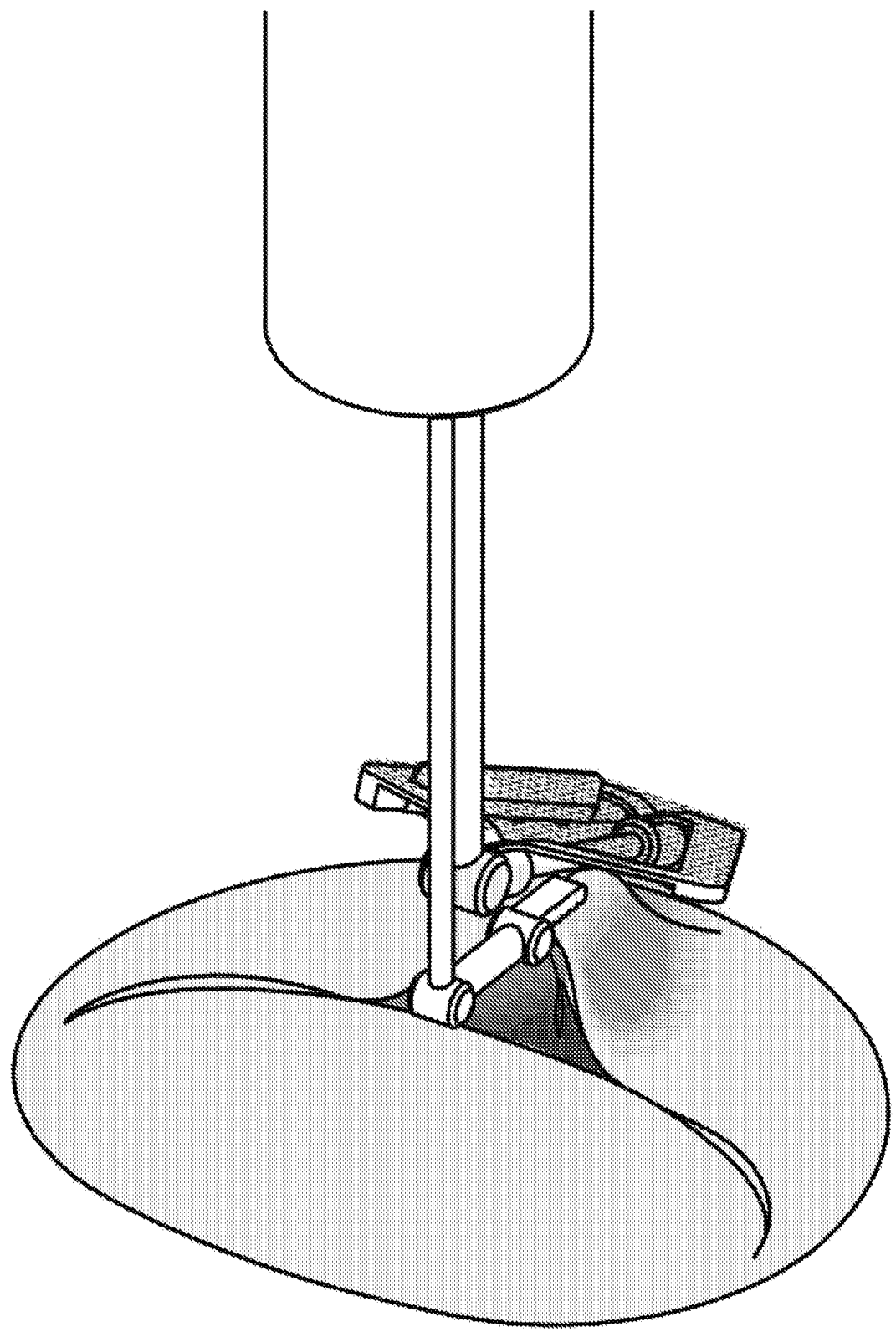
Fig. 5 b12

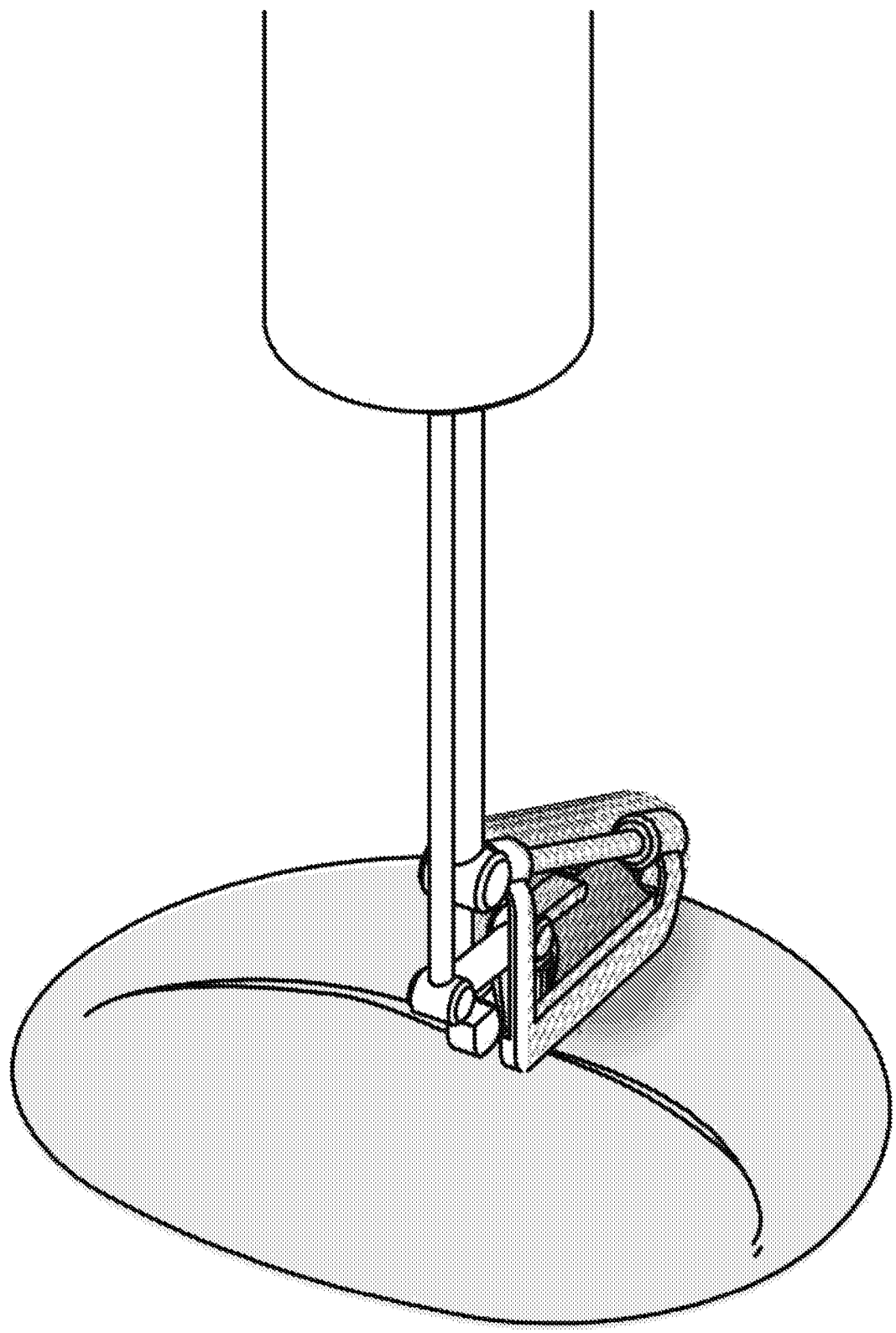
Fig. 5 b13

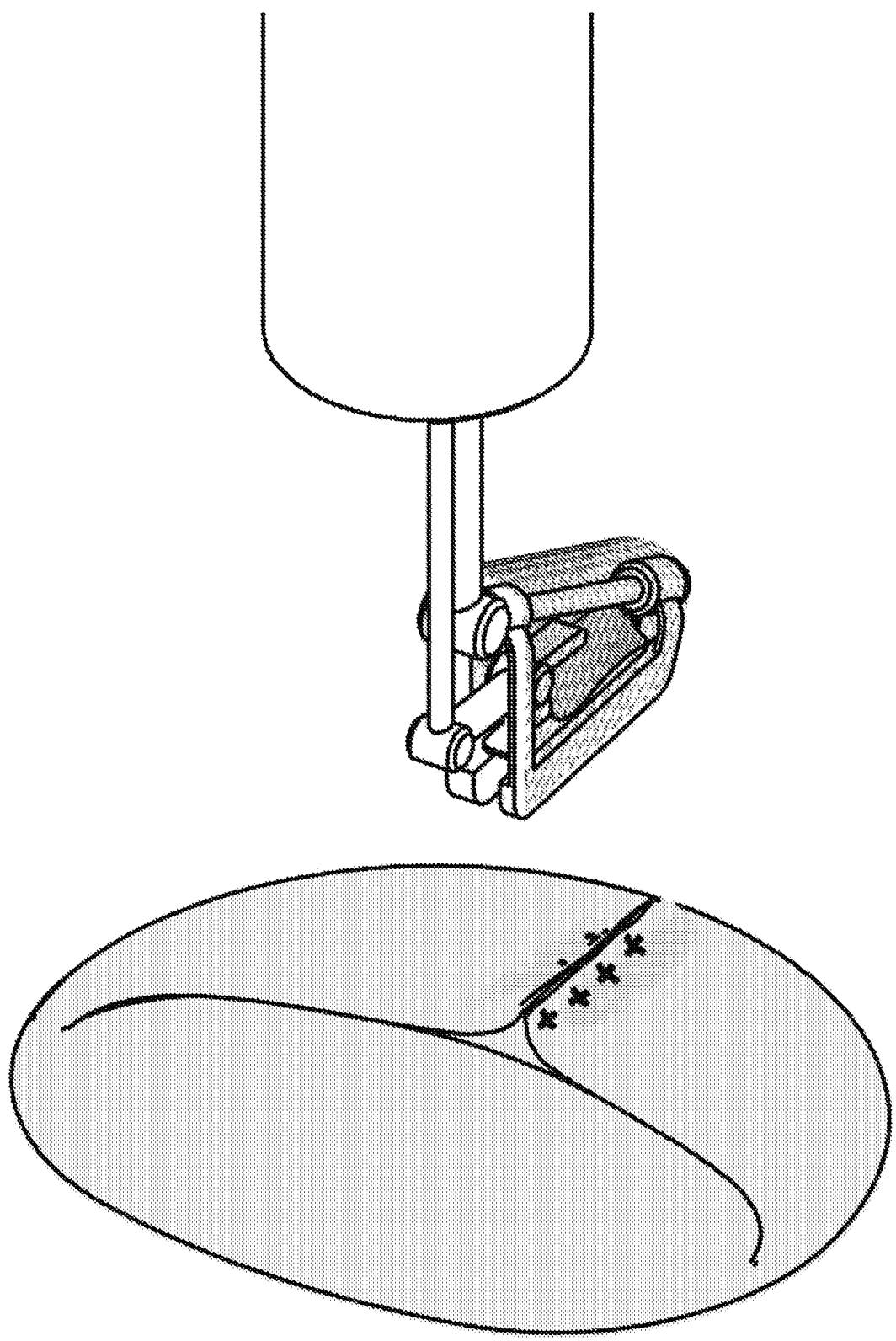
Fig. 5 b14

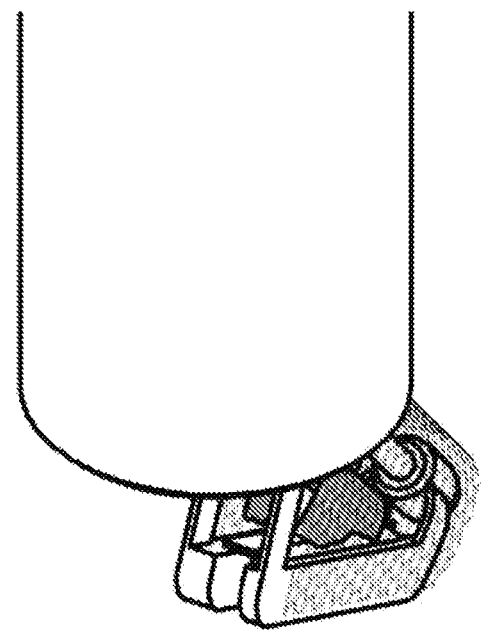
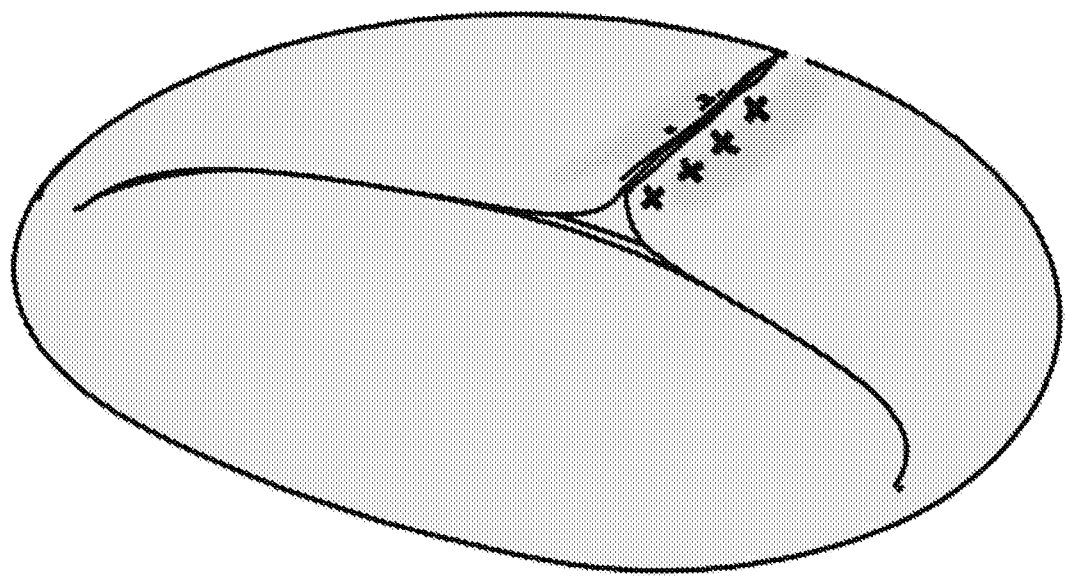
Fig. 5 b15

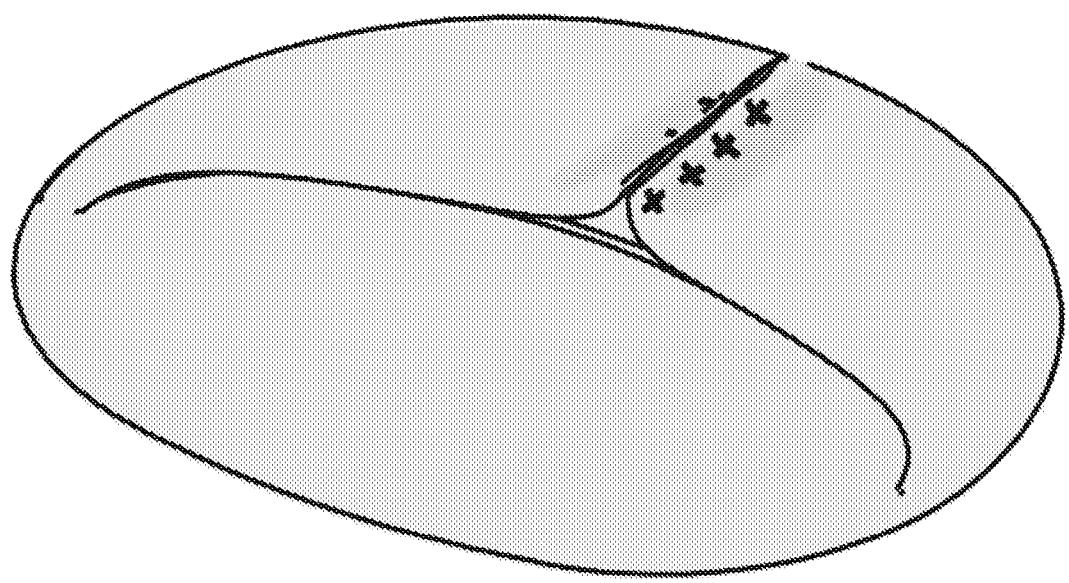
Fig. 5 b16

DEVICE AND METHOD FOR TRANSCATHETER HEART VALVE REPAIR UNDER TRIANGULAR RESECTION TECHNIQUE

CROSS REFERENCE TO RELATED APPLICATIONS

The present application is a U.S. national stage application of PCT/IB2016/050081 filed on Jan. 8, 2016 designating the United States, and claims foreign priority to International patent application PCT/IB2015/050227 filed on Jan. 12, 2015, and also claims foreign priority to the Swiss patent application CH00453/15 filed on Mar. 30, 2015, the contents of all three documents being herewith incorporated by reference in their entirety.

FIELD OF INVENTION

The present invention relates to heart valve repair, in particular mitral valve repair.

STATE OF THE ART

Mitral valve regurgitation (MR) is an abnormal, backwards flow of blood in the heart through the mitral valve. The mitral valve is one of 4 valves in the heart. It is located between the upper left heart chamber (left atrium) and lower left heart chamber (left ventricle). The mitral valve has 2 flaps, called leaflets, which open and close like a door with each heartbeat and normally let blood flow in just one direction through the heart. If the mitral valve does not close properly, some of the blood from the left ventricle is forced back up (regurgitated) into the left atrium instead of flowing out to the rest of the body. The added workload on the heart and increased blood pressure in the lungs may eventually cause problems. Although many diseases can damage the mitral valve and cause regurgitation mitral valve prolapse is the most frequent abnormality affecting 2.5% of the population. From that, 5 to 10% will develop severe regurgitation being the most common cause of mitral insufficiency in USA. Mitral valve prolapse occurs when the mitral valve leaflet tissue is deformed and elongated so that the leaflets do not come together normally leading to a MR. In severe cases, the left ventricle enlarges and functions less efficiently, the left atrium progressively enlarges, abnormal heart rhythms occur, and the blood pressure in the pulmonary artery increases leading to a pulmonary hypertension. Over time, these changes become irreversible as the signs and symptoms of heart failure develop.

Ischemic MR is a complication of coronary heart disease; it primarily occurs in patients with a prior myocardial infarction (MI). MR may also occur with acute ischemia, a setting in which the MR typically resolves after the ischemia resolves. Following an MI, the MR is usually due to infarction with permanent damage to the papillary muscle or adjacent myocardium; in such patients, MR may become more severe with adverse remodeling of the left ventricle or subsequent ischemia.

The need for treatment of MR depends upon the presence and severity of symptoms, the cause of the MR, and the presence of other underlying medical conditions. Medical and surgical therapies are available to treat people with MR. The treatment of choice for most people with severe chronic MR is surgical repair or replacement of the mitral valve.

The mortality and long term results depends directly of the preoperative clinical condition. In patients with impaired left ventricular function, pulmonary hypertension (very common in mitral regurgitation) the surgical risk can be over 10%. The clinical relevance to find alternative approaches, which do not involve cutting the sternum is enormous.

There is strong scientific evidences confirming that the repair instead replacement of the mitral valve is the treatment of choice mainly because its lower operative mortality and better long-term survival. Among the different techniques used to treat mitral prolapsed, the simplest and effective consists in resecting the prolapsed segment trough a triangular resection. This technique can be used in all types of prolapsed posterior leaflets an in many prolapsed anterior leaflets. This technique can be also used to treat ischemic MR.

International patent application WO 2006/007576 discloses a system for percutaneous tissue repair. This device may also be used for mitral valve repair. The tissue is grasped, plicated and then sewed.

With the system disclosed in WO 2006/007576 it is however not possible to carry out a triangular resection.

GENERAL DESCRIPTION OF THE INVENTION

The present invention provides a new and original solution to repair a heart valve, in particular a mitral valve, in a percutaneous manner and, preferably, based on a "triangular resection" technique.

The invention more precisely concerns a medical device and a surgical method for using said device as defined in the claims.

The method according to the invention can be applied to the posterior leaflets (P1, P2 and P3) as well as the anterior leaflet. It can be also applied to treat prolapsed aortic valves, and prolapsed tricuspid valves.

The method comprises the triangular plication of the prolapsed portion of the leaflet, the pinching of the plicated portion and, preferably, the resection of the excess of leaflet tissue.

The method is based on the use of a single catheter (however two catheters could also be used from different access, namely transatrial, transapical etc.) that is inserted through a trans-septal access via the femoral vein or a peripheral vein or a transatrial access or a transapical access via a small thoracotomy incision.

DETAILED DESCRIPTION OF THE INVENTION

To better disclose the invention, some illustrated but non-limiting examples are provided in the present chapter.

Figure 1:
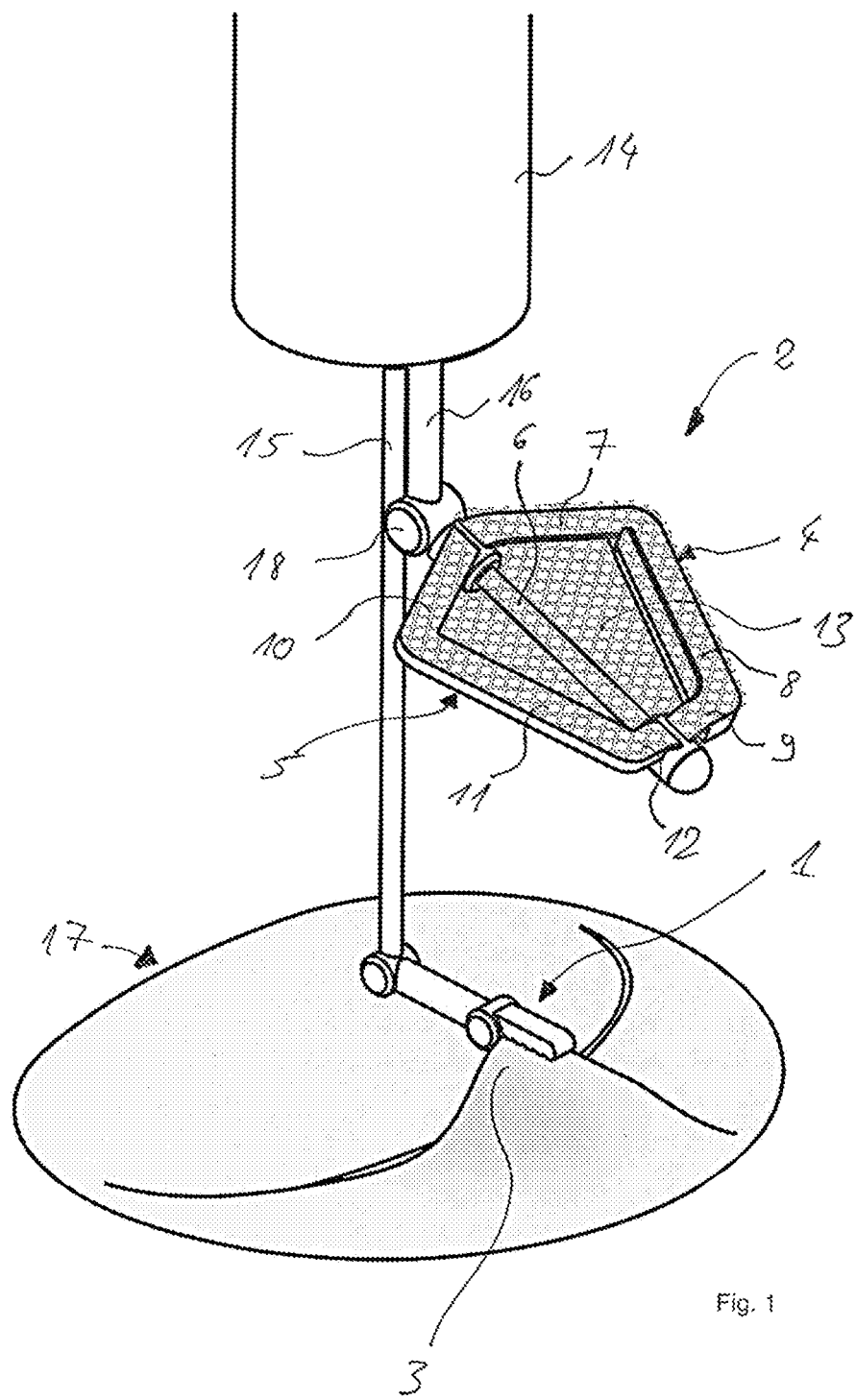
FIG. 1 illustrates a first example of a device according to the invention
Figure 2B:
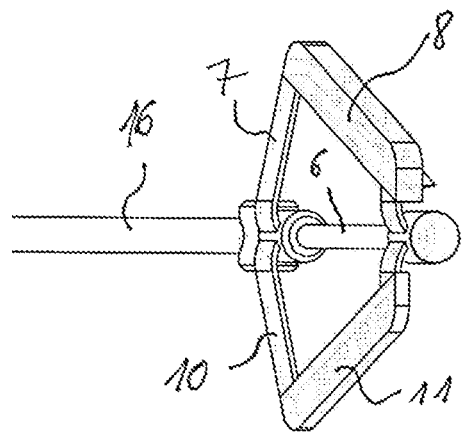
FIG. 2 illustrates the plicating tweezer of FIG. 1 in an open configuration and forming an angle of 25° with respect to the tweezer main axis.
Figure 2D:
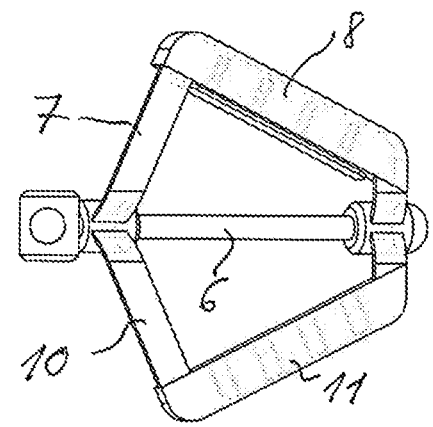
Figure 2A:
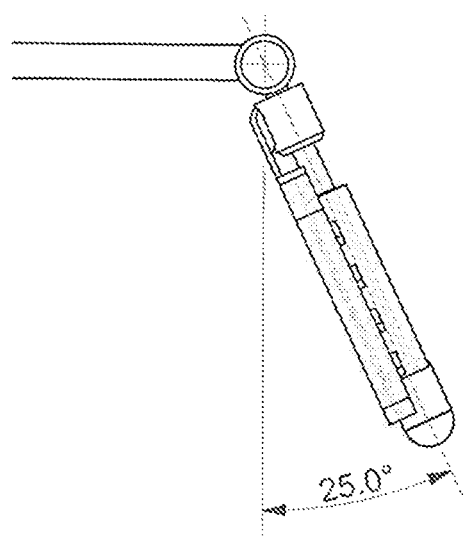
Figure 2C:
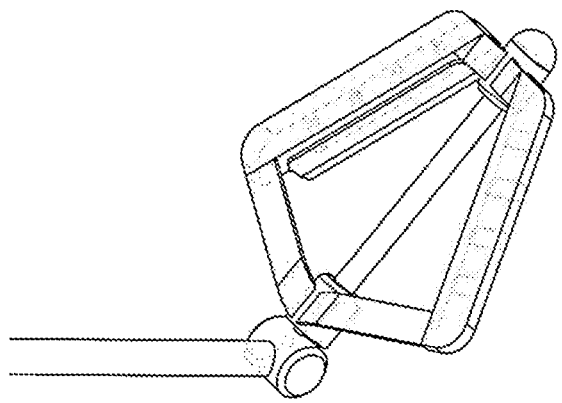
Figure 3C:
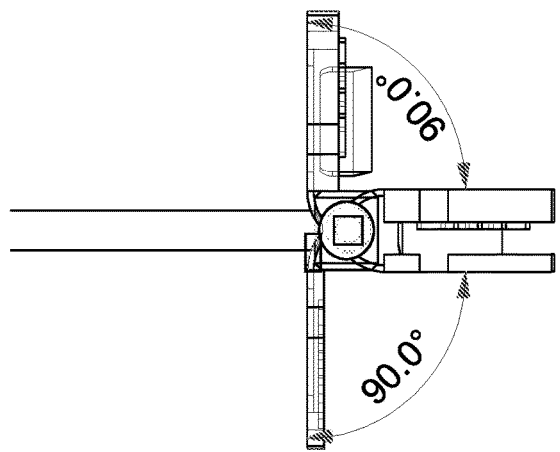
FIG. 3 illustrates the plicating tweezer of FIG. 1 in an open configuration and forming an angle of 90° with respect to the tweezer main axis.
Figure 3B:
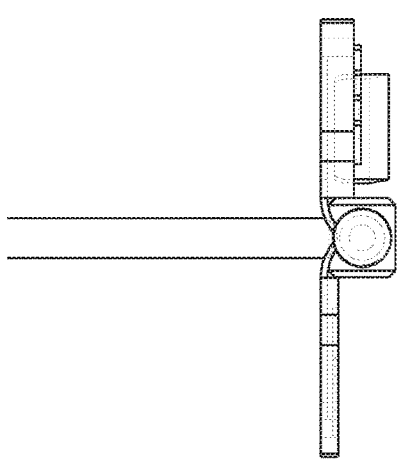
Figure 3E:
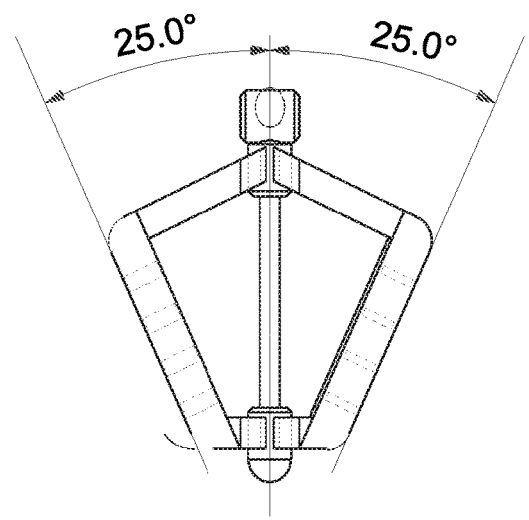
Figure 3A:
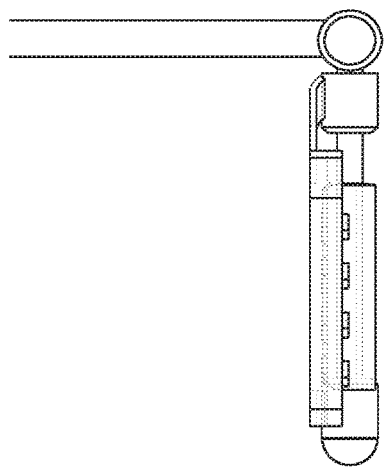
Figure 3D:
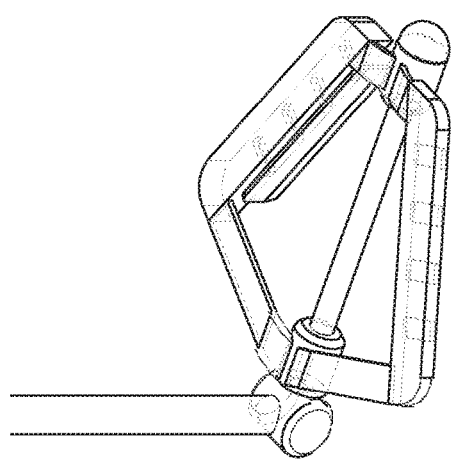
Figure 4B:
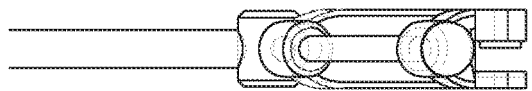
FIG. 4 illustrates the plicating tweezer of FIG. 1 in an closed configuration and forming an angle of 25° with respect to the tweezer main axis.
Figure 4D:
Figure 4A:
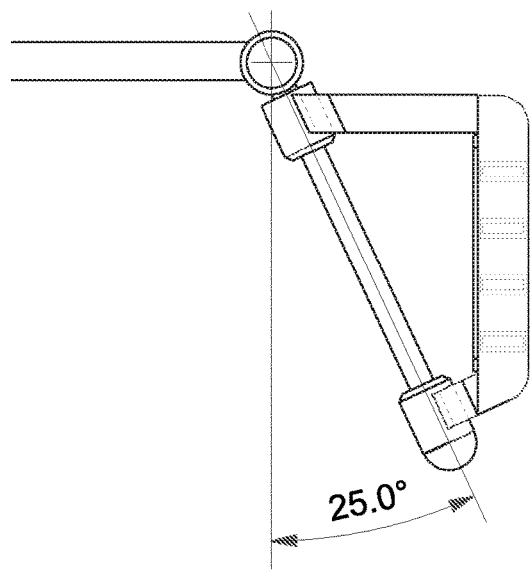
Figure 4C:
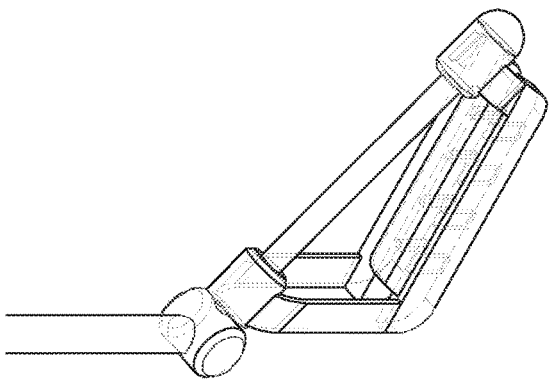

FIGS. 5a01 to 5a16 show different steps of one surgical method according to the invention, taken from a first point of view.

FIGS. 5b01 to 5b16 show different steps of the method illustrated in FIGS. 5a01 to 5a16, but taken from another point of view.

NUMERICAL REFERENCES USED IN THE FIGURES

1 Grasping tweezer
2 Plicating tweezer
3 Tissue prolapsed portion or tissue rim
4 First flap
5 Second flap
6 Central shaft
7 First long segment of first flap
8 Second long segment of first flap
9 Short segment of first flap
10 First long segment of second flap
11 Second long segment of second flap
12 Short segment of second flap
13 Mesh
14 Catheter
15 Grasping tweezer main axis
16 Plicating tweezer main axis
17 Mitral valve
18 Plicating tweezer rotation axis FIG. 1 illustrates a mitral valve 17 having a leaflet containing a prolapsed portion 3.

The device comprises a tissue grasping tweezer 1 and a plicating tweezer 2, both tweezers 1,2 are moved to the operating field within a single catheter 14.

The grasping tweezer 1 forms a variable angle with respect to the grasping tweezer main axis 15.

The plicating tweezer 2 is made of a central shaft 6 around which two triangular shaped flaps 4,5 can rotate. Each flap 4,5 comprises two main segments 7,8,10,11 which, together with the central shaft 6, form a triangular element. All the segments 7-12 are furthermore covered by a mesh 13.

In addition, or in replacement to the mesh 13, the segments 7-12 may be covered by a metallic layer, a synthetic layer or a biological tissue.

The catheter 14 is inserted at the level of the diseased valve 17 in correspondence of the prolapsed portion of the leaflet 3 (FIG. 5a01, FIG. 5a02, FIG. 5b01 and FIG. 5b02). The grasping tweezer 1 is extracted from the catheter 14 and under fluoroscopy and Echo 3D guidance is remotely actuated by the operator in a way to grab the central portion of the prolapsed portion 3 for an extension going from the free edge towards the mitral annulus (typically a length ranging from 0.5 to 2.5 cm) (FIGS. 5a03 to a08 and FIGS. 5b03 to b08).

The plicating tweezer 2 is then extracted from the catheter 14, rotated around an axis 18, opened and placed parallel to an ideal valve plan, in touch with the prolapsed portion 3 (FIGS. 5a09 to a12 and FIGS. 5b09 to b12).

When the device is stable the grasping tweezer 1, still grabbing the prolapsed portion 3, is moved slightly upward creating a tensioned flap corresponding to the prolapsed portion 3. In this setting the plicating tweezer 2 is closed, over the grasping tweezer 1, to plicate and pinching triangular shaped prolapsed portion 3 (FIG. 5a13 and FIG. 5b13).

At this stage, before to proceed cutting out the prolapsed portion 3, the online control with an Echo 2D or better 3D may confirm that the residual regurgitation is negligible or eliminated.

If the hemodynamic conditions of the mitral valve 17 are considered suboptimal the procedure can be repeated retracting the plicating tweezer 2 and using the grasping tweezer 1 to pinch more or less leaflet tissue or to slightly change position to better pinch the prolapsed portion 3. When the grasping tweezer 1 pinches the leaflet again the procedure can be allover repeated.

The plicating tweezer 2, when open, has a polygonal shape (FIG. 5a11) made by a plurality of segments 6-12 which substantially form two triangular frames hinged at level of the central shaft 6. More precisely, each substantial triangular frame is formed by three long segments 6-8 & 6,10,11 (that form the general triangular shape) and one short segment 9,12. The shape and dimensions of the triangular frames can be variable in order to treat a different degree of leaflet prolapse. A thin mesh of tissue 13 made of biological, polymeric or metallic material covers the triangular frames. The purpose of the mesh coverage is to avoid the accidental embolization of blood clots, calcific fragments or leaflet's portions during the transcatheter mitral repair procedure.

Once a satisfactory result is reached the arms of the plicating tweezer 2 are closed over the folded prolapsed leaflet 3. The flap sides 8,11 of the plicating tweezer 2 which are in contact with the tissue can deliver a series of staples, stitches, thermal treatment, radiofrequency, cryo-therapy treatment or any other system to fix together the two portions of the prolapsed leaflet 3. In alternative constructive solution the portions of the leaflet could be glued together by injecting glue, polymers or any other biocompatible glue material through the arms of the tweezer (FIG. 5a12, a13 and FIG. 5b12, b13).

The pinched leaflet portion will be on the atrial side however the repair procedure could be also performed upside down in a way that the pinched portion of the leaflet is oriented toward the ventricle and placed below the valve plane. This is useful especially, but not exclusively, in patients with complete flail (complete chordae rupture).

The procedure can be completed with the resection of the plicated and pinched portion in both the above-described procedural situations. The flap sides 8,11 of the plicating tweezer 2 which are in contact with the tissue are equipped with a system making a triple function. One is aimed at locking the base line of the plicated, triangular shape, portion of the leaflet, the second one to deliver staples or stitches and the third one at cutting the plicated leaflet portion just above the suture line (FIG. 5a14, FIG. 5b14).

At the end of the procedure the arms of the plicating tweezer 2 are maintained closed over the leaflet tissue fragment and retrieved into the catheter together with the first tweezer (FIG. 5a15, FIG. 5 b15).

The procedure is completed when the entire catheter is fully retrieved out of the patient (FIG. 5a16, FIG. 5 b16).

Both tweezers 1,2 can be realized with different materials including various metals alloys such as Nitinol, Stainless steel, Cobalt-Chromium or plastic polymers. The articulation and the remote control of the tweezers can be realized adopting several mechanical, pneumatic, hydraulic or electrical solutions also using memory shape alloys such as the Nitinol. The arms of the tweezers 1,2 can be straight or curved with different length depending the final adopted solution.

One way to perform the "plication" is achieved with a surgical stapler together with surgical staples. The staple line may be straight, curved or circular. The instruments may be used in either open or thoracoscopic surgery or full transcatheter, and different instruments can be used for each application. Transcatheter staplers must be longer, thinner, and may be articulated to allow for access from the peripheral veins or arteries.

Some device can incorporate a knife, to complete excision of the prolapsed segment of the mitral leaflet and anastomosis in a single operation.

The surgical staples can be made of titanium, namely a material that induces less reaction with the immune system and, being non-ferrous, does not interfere significantly with MRI scanners. Synthetic absorbable or non-absorbable materials could also be used.

The invention is of course not limited to the device presented in the previous example. The device according to the invention may be used for plication only, i.e. without removal of the prolapsed part of the leaflet.

The invention claimed is:

1. A medical device for transcatheter heart valve repair comprising: a grasping tweezer configured to grasp a leaflet rim to form a prolapsed portion; and a plicating tweezer including two rotatable flaps and a central shaft defining a longitudinal axis of the plicating tweezer, wherein each flap has a substantially triangular shape, wherein a first side of a triangle that forms the triangular shape is defined by the central shaft, a second side is located on a proximal end of the plicating tweezer, and a third side is located on a distal end of the plicating tweezer, wherein the second and third sides define a free end for each flap, the free ends of the rotatable flaps configured to approach each other upon turning the rotatable flaps around the central shaft towards each other, and the free ends configured to distance themselves from each other upon turning the rotatable flaps around the central shaft away from each other.

2. The medical device according to claim 1, wherein the central shaft and the third side form an angle between 0° and 90°.

3. The medical device according to claim 2, wherein the angle is between 15° and 35°.

4. The medical device according to claim 1, wherein each flap includes a plurality of segments.

5. The medical device according to claim 4, wherein the plurality of segments are covered by a mesh.

6. The medical device according to claim 1, wherein at least one flap includes a releasable tissue fixing device.

7. The medical device according to claim 1, wherein at least one flap includes a tissue-cutting device.

8. The medical device according to claim 1, wherein the central shaft is made rotatable with respect to a main axis of the plicating tweezer.

9. The medical device according to claim 6, wherein the releasable tissue fixing device includes staples.

10. A method for using a medical device for transcatheter heart valve repair, the medical device including a grasping tweezer configured to grasp a leaflet rim of a leaflet, and a plicating tweezer including two rotatable flaps having free ends and a central shaft around which the free ends of the two rotatable flaps are configured to rotate in a butterfly manner such that the plicating tweezer can adopt a closed configuration or an open configuration, the method comprising the steps of:
grasping and pulling the leaflet rim by the grasping tweezer to form a prolapsed portion; and
triangular plicating the prolapsed portion of the leaflet with the free ends of the two rotatable flaps of the plicating tweezer to form a plicated region.

11. The method according to claim 10, further comprising the steps of:
cutting the plicated region of the leaflet; and
removing the plicated region.

12. The medical device according to claim 1, wherein the free ends of the two rotatable flaps of the plicating tweezer are configured to hold the prolapsed portion of the leaflet to form a plicated region while the grasping tweezer is configured to hold the prolapsed portion.

13. The medical device according to claim 1, wherein while the grasping tweezer is configured to hold the prolapsed portion of the leaflet rim, the plicating tweezer is configured to be moved to the leaflet such that the two rotatable flaps can fold over the grasping tweezer to form the closed configuration.

14. The medical device according to claim 1, wherein the plicating tweezer further includes a main axis, the main axis and the central shaft configured to pivot relative to each other.

* * * * *